United States Patent [19]

Vandenberk et al.

[11] 4,377,578

[45] Mar. 22, 1983

[54] PIPERAZINE DERIVATIVES

[75] Inventors: Jan Vandenberk, Beerse; Ludo E. J. Kennis, Vosselaar; Marcel J. M. C. Van der Aa, Vosselaar; Albert H. M. Th. Van Heertum, Vosselaar, all of Belgium

[73] Assignee: Janssen Pharmaceutica, N.V., Beerse, Belgium

[21] Appl. No.: 286,438

[22] Filed: Jul. 24, 1981

Related U.S. Application Data

[60] Continuation of Ser. No. 88,703, Oct. 26, 1979, abandoned, which is a division of Ser. No. 875,342, Feb. 6, 1978, Pat. No. 4,200,641, which is a continuation of Ser. No. 753,062, Dec. 21, 1976, abandoned, which is a continuation-in-part of Ser. No. 672,919, Apr. 2, 1976, abandoned.

[51] Int. Cl.$^3$ .................. A61K 31/495; C07D 403/06
[52] U.S. Cl. ..................................... 424/250; 544/370
[58] Field of Search ........................ 544/370; 424/250

[56] References Cited

U.S. PATENT DOCUMENTS

3,362,956  1/1968  Archer .................................. 544/370
3,472,854  10/1969  Archer .................................. 544/370

*Primary Examiner*—Paul M. Coughlan, Jr.
*Attorney, Agent, or Firm*—Geoffrey G. Dellenbaugh

[57] ABSTRACT

Novel 1-substituted 4-(diarylmethyl)piperazine derivatives having antianaphylactic and antihistaminic properties.

6 Claims, No Drawings

PIPERAZINE DERIVATIVES

CROSS-REFERENCE TO RELATED APPLICATIONS

This application is a continuation of our copending application Ser. No. 088,703, filed Oct. 26, 1979, now abandoned, which in turn is a division of application Ser. No. 375,342, filed Feb. 6, 1978, now U.S. Pat. No. 4,200,641, which in turn is a continuation of application Ser. No. 753,062, filed Dec. 21, 1976, now abandoned, which in turn is a continuation-in-part of application Ser. No. 672,919, filed Apr. 2, 1976, now abandoned.

BACKGROUND OF THE INVENTION

In the prior art there may be found a number of 1-[(heterocyclyl)alkyl]piperazines and a number of 1-substituted 4-(diarylmethyl)piperazine and 4-(diarylmethoxy)piperidine derivatives having pharmacological properties. Such compounds are described in the following references:
U.S. Pat. No. 3,362,956;
U.S. Pat. No. 3,472,854;
U.S. Pat. No. 3,369,022;
U.S. Pat. No. 2,882,271;
U.S. Pat. No. 3,956,328; and
C.A., 64, 3499e (1966).

The compounds of this invention differ from the foregoing essentially by the nature of the B—$C_nH_{2n}$-group, present in the 1-position of the piperazine or piperidine group, and/or by the nature of the diarylmethyl or diarylmethoxy group present in the 4-position of said piperazine, respectively piperidine group.

DESCRIPTION OF THE PREFERRED EMBODIMENTS

This invention relates to novel chemical compounds and more particularly to piperazine and piperidine derivatives which may structurally be represented by the formula:

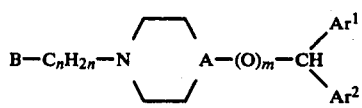 (I)

and the pharmaceutically acceptable acid addition salts thereof, wherein:
Ar$^1$ and Ar$^2$ are each independently selected from the group consisting of phenyl, substituted phenyl and pyridinyl, wherein said substituted phenyl is phenyl having from 1 to 2 substituents independently selected from the group consisting of halo, lower alkyl, lower alkyloxy, trifluoromethyl and nitro;
m is the integer zero or 1;
A is a member selected from the group consisting of

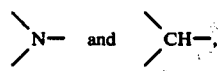

provided that when said A is

then said m is zero and when said A is

then said m is 1;
n is an integer of from 2 to 6 inclusive, provided that when $C_nH_{2n}$ represents a branched alkylene chain, then at least 2 carbon atoms are present in the linear portion of the chain linking B with the piperidine or piperazine nitrogen atom; and
B is a member selected from the group consisting of:
(a) a radical having the formula

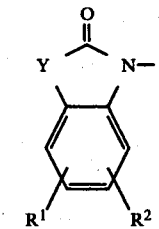

wherein:
R$^1$ and R$^2$ are each independently selected from the group consisting of hydrogen, halo, lower alkyl and trifluoromethyl; and
Y is a member selected from the group consisting of oxygen, sulfur and a substituted nitrogen of the formula

wherein said L is a member selected from the group consisting of hydrogen, lower alkyl, lower alkylcarbonyl, lower alkyloxycarbonyl-lower alkyl, carboxy-lower alkyl, phenyl, phenylmethyl, lower alkylaminocarbonyl, hydroxymethyl, and lower alkenyl; and
(b) a radical having the formula

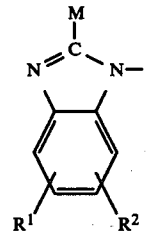

wherein:
R$^1$ and R$^2$ are each independently selected from the group consisting of hydrogen, halo, lower alkyl, and trifluoromethyl; and M is a member selected from the group consisting of hydrogen, lower alkyl, phenyl, phenylmethyl, mercapto, lower alkylthio, amino, lower alkylcarbonylamino, lower alkyloxycarbonylamino, and cycloalkyl having from 3 to 6 carbon atoms.

As used in the foregoing and in the following definitions, "lower alkyl" is meant to include straight and branch chained hydrocarbon radicals having from 1 to 6 carbon atoms such as, for example, methyl, ethyl, 1-methylethyl, 1,1-dimethylethyl, propyl, butyl, pentyl, hexyl and the like; "lower alkenyl" is meant to include straigth and branch chained alkenyl radicals having from 2 to 6 carbon atoms such as, for example, ethenyl, 1-methylethenyl, 1-propenyl, 2-propenyl, 2-butenyl, 1-methyl-2-butenyl, 2-pentenyl, 2-hexenyl and the like; "cycloalkyl" refers to cyclic hydrocarbon radicals having from 3 to 6 carbon atoms such as, for example, cyclopropyl, cyclobutyl, cyclopentyl and cyclohexyl; the expression "$C_nH_{2n}$" refers to straight and branch chained alkylene chains having from 2 to 6 carbon atoms and having at least 2 carbon atoms in the linear portion of the chain linking the B-group with the piperidine or piperazine nitrogen, such as, for example, 1,2-ethanediyl, 1,3-propanediyl, 2-methyl-1,3-propanediyl, 1,4-butanediyl, 2-methyl-1,4-butanediyl, 1,5-pentanediyl, 1,6-hexanediyl and the like; and the term "halo" is generic to halogens of atomic weight less than 127, i.e., fluoro, chloro, bromo and iodo.

The subject compounds of formula (I), except those wherein B stands for a 2-amino-1H-benzimidazol-1-yl radical, may conveniently be prepared by reacting an appropriate reactive ester of formula (II) wherein n is as previously defined, B is as previously defined except a 2-amino-1H-benzimidazol-1-yl radical of the formula

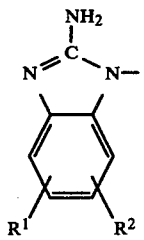

wherein $R^1$ and $R^2$ are as previously defined, and W is an appropriate reactive ester function derived from the corresponding alcohol such as, for example, halo, methanesulfonyl, 4-methylbenzenesulfonyl and the like, with an appropriate piperidine or piperazine derivative of formula (III) wherein A, m, $Ar^1$ and $Ar^2$ are as previously defined:

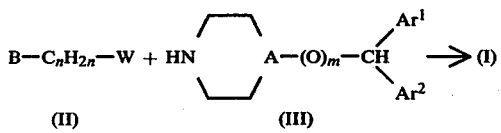

The foregoing condensation reaction is preferably carried out in an appropriate reaction-inert organic solvent such as, for example, a lower alkanol, e.g. methanol, ethanol, propanol, butanol and the like alkanols; an aromatic hydrocarbon, e.g., benzene, methylbenzene, dimethylbenzene and the like; an ether, e.g., 1,4-dioxane, 1,1'-oxybispropane and the like; a ketone, e.g., 4-methyl-2-pentanone; N,N-dimethylformamide; nitrobenzene; and the like. The addition of an appropriate base such as, for example, an alkali metal or earth alkali metal carbonate or hydrogen carbonate, may be utilized to pick up the acid which is liberated during the course of the reaction. A small amount of an appropriate metal iodide, e.g., sodium or potassium iodide may be added as a reaction promotor. Somewhat elevated temperatures are appropriate to enhance the rate of the reaction and preferably the reaction is carried out at the reflux temperature of the reaction mixture.

In this and following preparations, the reaction products are separated from the reaction mixture and, if necessary, further purified by the application of methodologies generally known in the art.

The compounds of formula (I) wherein B stands for a 2-amino-1H-benzimidazol-1-yl radical, (I-a), are easily prepared starting from the corresponding compounds (I) wherein B stands for a 2-(lower alkyloxycarbonylamino)-1H-benzimidazol-1-yl radical, (I-b), by decarboxylating the latter under hydrolytic conditions, for example, by acid hydrolysis using an appropriate strong acid, such as hydrochloric, hydrobromic or sulfuric acid, or by alkaline hydrolysis using an appropriate strong base such as, for example, sodium or potassium hydroxide.

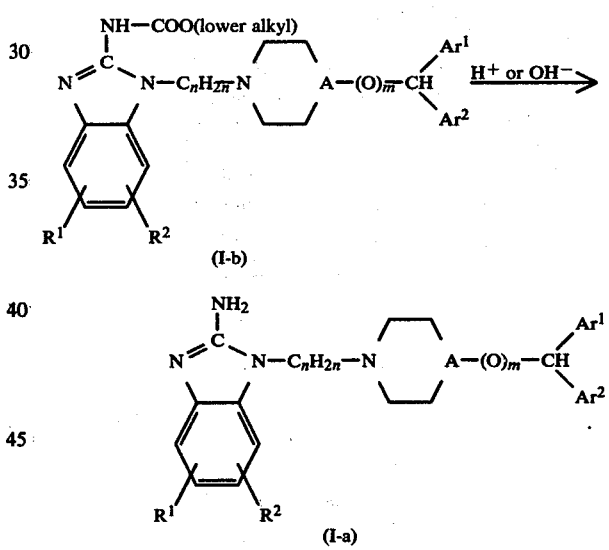

It is to be noted that when the B-group in compounds of formula (I) or in intermediates therefor stands for a 2-(lower alkyloxycarbonylamino)-1H-benzimidazol-1-yl or a 2-(lower alkylcarbonylamino)-1H-benzimidazol-1-yl radical, then said radicals may exist in different tautomeric forms as is illustrated hereafter:

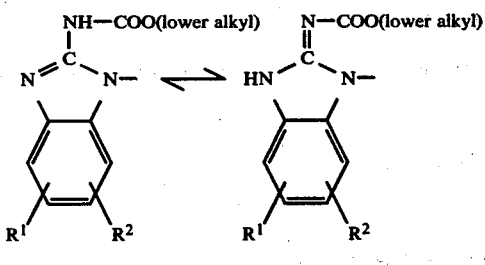

-continued

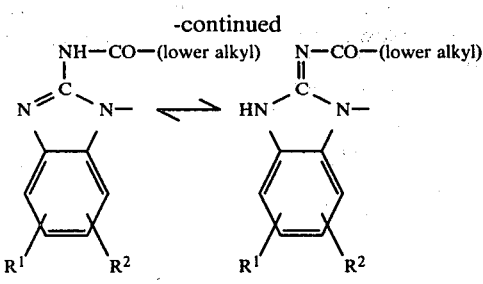

Such tautomeric forms of compounds of formula (I) are naturally intended to be within the scope of this invention.

Compounds of formula (I) which may be represented by the formula (I-c):

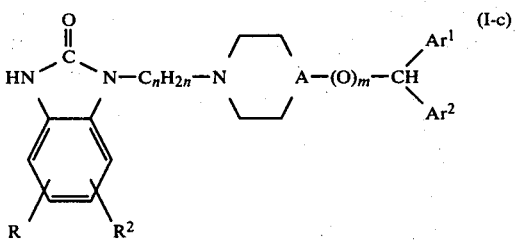

wherein $R^1$, $R^2$, n, A, $Ar^1$ and $Ar^2$ are as previously defined may alternatively be prepared by ring closure of an appropriate intermediate of formula (IV) with an appropriate cyclizing agent as known in the art for the preparation of 1,3-dihydro-2H-benzimidazol-2-ones starting from 1,2-benzenediamines.

Suitable cyclizing agents which may advantageously be employed include, for example, urea, carbonyl dichloride and alkali metal isocyanates, and the cyclization reaction may be performed following methodologies generally known in the art. For example, when urea is used as the cyclizing agent the compounds (I-c) are easily obtained by stirring and heating the reactants together in the absence of any solvent.

The foregoing preparations may be illustrated as follows.

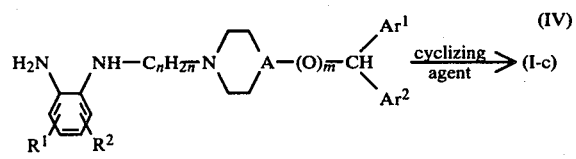

The compounds of formula (I-c) may still be prepared starting from the corresponding compounds of formula (V)

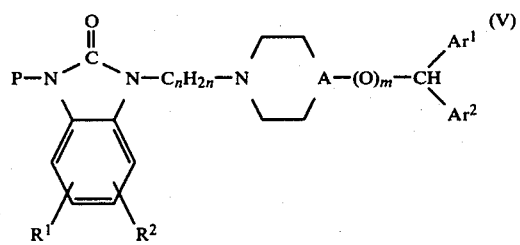

wherein $R^1$, $R^2$, n, A, m, $Ar^1$ and $Ar^2$ are as previously defined and P is an appropriate protecting group, by the removal of said protecting group according to conventional procedures. As examples of such protecting groups there may be mentioned lower alkyloxycarbonyl and, a substituted ethenyl group of the formula

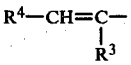

wherein $R^3$ and $R^4$ may represent different groups but wherein $R^3$ is preferably lower alkyl and $R^4$ is preferably hydrogen, lower alkyl or phenyl.

When the protecting group is lower alkyloxycarbonyl, it may easily be removed by alkaline hydrolysis, and when the protecting group is a substituted ethenyl group it is conveniently eliminated by subjecting the appropriate intermediate (V) to acid hydrolysis. In carrying out the acid hydrolysis to remove the substituted ethenyl group from (V) a wide variety of protonic acids may be employed, including mineral acids such as, for example, hydrochloric, hydrobromic, sulfuric, nitric and phosphoric acid, and organic acids such as, for example, acetic, propanoic, ethanedioic and the like acids. Further the reaction may be carried out in reaction-inert organic solvents as commonly employed in such a type of hydrolytic reactions, e.g., lower alkanols such as, for example, methanol, ethanol, 2-propanol and the like.

In a procedure similar to that described for the preparation of the compounds (I-c) starting from (IV) there may also be prepared compounds of the formula (I-d)

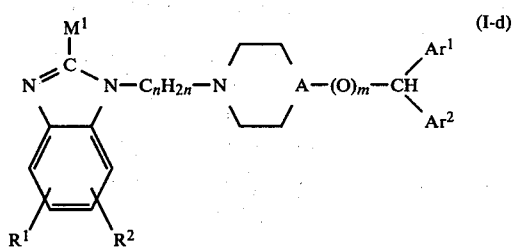

wherein $R^1$, $R^2$, n, A, m, $Ar^1$ and $Ar^2$ are as previously defined, and $M^1$ is selected from the group consisting of hydrogen, lower alkyl, phenyl, phenylmethyl, mercapto, amino, lower alkyloxycarbonylamino and cycloalkyl, by the reaction of (IV) with an appropriate cyclizing agent, following art-known methodologies of preparing 1H-benzimidazoles starting from 1,2-benzenediamines. Depending on the nature of $M^1$ in the compounds (I-d) the following cyclizing agents may, for example, be employed.

When $M^1$ stands for hydrogen there may be used formic acid or an appropriate tri(alkyloxy)methane as a cyclizing agent.

When $M^1$ stands for lower alkyl, phenyl, phenylmethyl or cycloalkyl, one may use a carboxylic acid of the formula

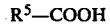

wherein $R^5$ is lower alkyl, phenyl, phenylmethyl, or cycloalkyl, or a functional derivative thereof such as, for example, an acyl halide, an ester, an amide or a nitrile derived from such acid or an iminoester of the formule

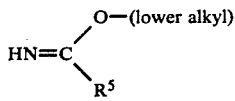

(VII)

wherein R⁵ is as defined hereabove; or an aldehyde of the formula

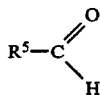

(VIII)

or an addition product thereof with an alkali metal hydrogen sulfite. When the cyclizing agent is an aldehyde there may be added to the reaction mixture an appropriate oxidizing agent such as, for example, nitrobenzene, mercuric oxide, Cu(II) and Pb (II) salts or other suitable oxidants as known in the art, or the aldehyde itself, when added in excess, may serve as an oxidant.

When M¹ stands for mercapto there may be used cyclizing agents such as, for example, carbon disulfide, thiourea, carbonothioic dichloride, ammonium thiocyanate and the like.

When M¹ is an amino group, ring closure may be performed with cyanamide, or a metal salt thereof, preferably an alkali or earth alkali metal salt, or with BrCN.

When M¹ stands for lower alkyloxycarbonylamino, one may use as a cyclizing agent, for example, an appropriate lower alkyl (iminomethoxymethyl)carbamate of the formula (IX)

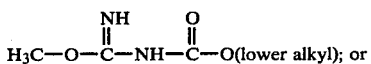

a lower alkyl [(lower alkoxycarbonylamino)(R⁶-thio)-methylene]carbamate of the formula (X)

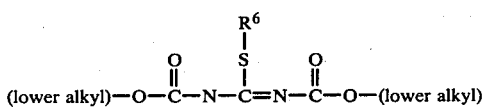

wherein R⁶ is hydrogen or methyl; or a lower alkyl carbonoisothiocyanatidate of the formula (XI)

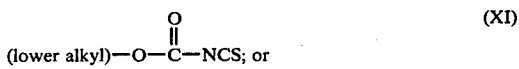

a lower alkyl lower alkylcarbamothioate of the formula (XII)

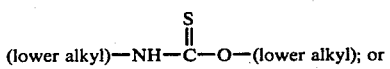

a dilower alkyl cyanimidodicarbonate of the formula (XIII)

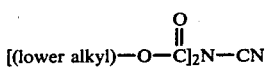

The foregoing cyclization reactions may all be performed following well-known methodologies as described in the literature.

Compounds of the formula (I-e)

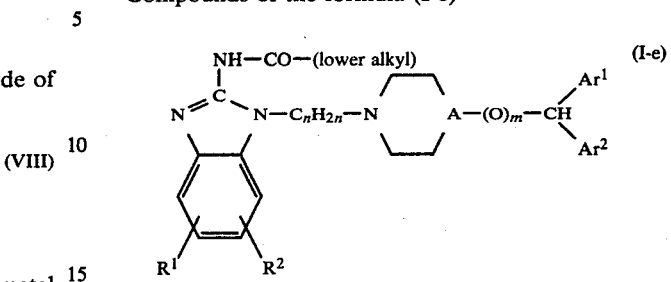

may alternatively be prepared by the acylation of an appropriate 2-amino-1H-benzimidazol-1-yl derivative of formula (I-a) following standard N-acylating procedures, e.g., by the reaction of (I-a) with an appropriate lower alkylcarbonyl halide or with an anhydride derived from a lower alkylcarboxylic acid.

Compounds of the formula (I-f)

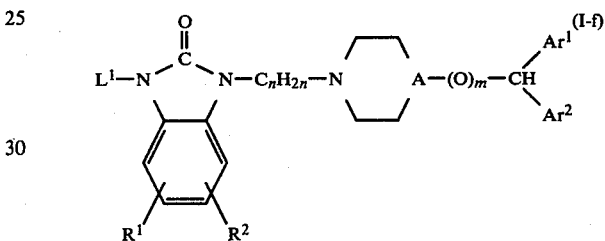

wherein R¹, R², n, A, m, Ar¹ and Ar² are as previously defined and L¹ is selected from the group consisting of lower alkyl, lower alkylcarbonyl, lower alkyloxycarbonyl-lower alkyl, carboxy-lower alkyl, phenylmethyl, lower alkylaminocarbonyl, hydroxymethyl and lower alkenyl, provided that the unsaturation in said lower alkenyl is located in a position other than α, may still be prepared by the introduction of said L¹ into a compound of formula (I-c)

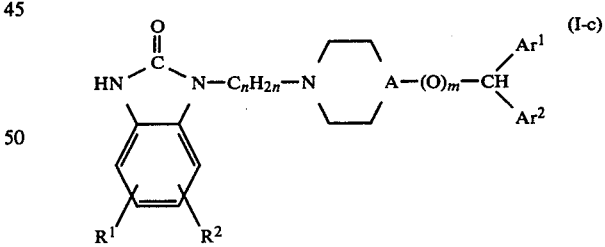

Depending on the nature of the L¹ group to be introduced the following methods may be utilized therefor.

When L¹ stands for lower alkyl, lower alkyloxycarbonyl-lower alkyl, phenylmethyl or lower alkenyl, in which case the symbol L¹ₐ is used therefor, the introduction of said L¹ₐ into (I-c) may be performed by the reaction of (I-c) with an appropriate reactive ester of the formula L¹ₐ-W, (XIV), wherein L¹ₐ is as defined hereabove and W has the same meaning as assigned to it in the definition of the starting materials of formula (II).

The condensation of (XIV) with (I-c) may be carried out under similar conditions as described hereinbefore for the condensation of the reactive esters (II) with the intermediates of formula (III). In order to enhance the reaction rate it may be appropriate in some instances to add to the reaction mixture a small amount of an appropriate macrocyclic polyether such as, for example, 2,3,11,12-dibenzo-1,4,7,10,13,16-hexaoxacyclooctadeca-2,11-diene as a reaction promotor.

When the $L^1$ group to be introduced is lower alkyloxycarbonylethyl, the introduction of said group may alternatively be performed by reacting (I-c) with a (lower alkyl) 2-propenoate of formula (XV)

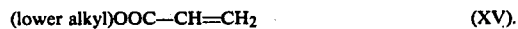

Said reaction may conveniently be carried out in a reaction-inert organic solvent such as, for example, an aromatic hydrocarbon, e.g., benzene, methylbenzene, dimethylbenzene and the like; an ether, e.g., 1,1'-oxybisethane, 2,2'-oxybispropane, tetrahydrofuran, 1,4-dioxane and the like, preferably in the presence of an appropriate aminium hydroxide such as, for example, N,N,N-triethylbenzenemethanaminium hydroxide.

Compounds of formula (I-f) wherein $L^1$ stands for carboxy-lower alkyl can easily be derived from the corresponding lower alkyloxycarbonyl-lower alkyl substituted compunds by hydrolyzing the latter in the usual manner, e.g., with aqueous alkali, to liberate the acid from the ester.

When the $L^1$ group is lower alkylcarbonyl said group may conveniently be introduced by the reaction of (I-c) with an appropriate acylating agent derived from the corresponding lower alkylcarboxylic acid such as, for example, a halide, preferably the chloride, or an anhydride, following standard N-acylating procedures.

When $L^1$ stands for lower alkylaminocarbonyl it may be introduced by the reaction of (I-c) with an appropriate isocyanatoalkane in an appropriate reaction-inert organic solvent such as, for example, an ether, e.g., 1,1'-oxybisethane, 2,2'-oxybispropane, 1,4-dioxane and the like.

When $L^1$ is a hydroxymethyl group its introduction is conveniently performed by the reaction of (I-c) with formaldehyde in an appropriate organic solvent such as, for example, N,N-dimethylformamide.

Compounds of the formula (I-g)

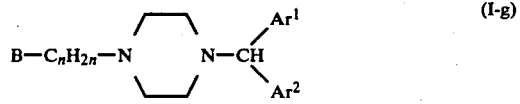

wherein B, n, $Ar^1$ and $Ar^2$ are as previously defined may alternatively be prepared by the condensation of a piperazine derivative of formula (XVI) with an appropriate reactive ester of formula (XVII) wherein $Ar^1$, $Ar^2$ and W are as previously defined, under similar conditions as described hereinbefore for the preparation of the compounds (I) starting from (II) and (III).

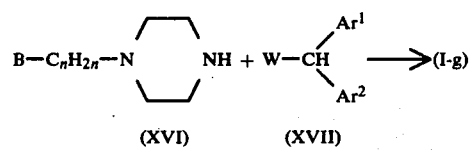

Compounds of the formula (I-h)

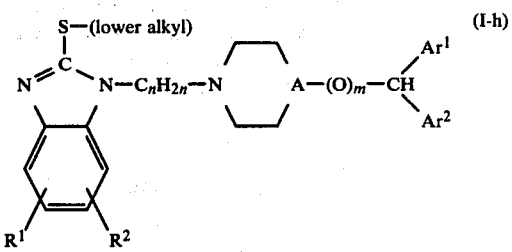

are also conveniently prepared starting from the corresponding -SH substituted analogs by standard S-alkylating procedures, e.g., by the reaction of the mercapto compound with an appropriate halo-lower alkane in an appropriate organic solvent such as, for example, a lower alkanol, e.g., ethanol, propanol, 2-propanol, butanol and the like.

A number of the intermediates of formula (II) are known compounds and some of them are described in U.S. Pat. Appln. Ser. No. 597,793, filed July 21, 1975 and in U.S. Pat. Appln. Ser. No. 620,727, filed Oct. 8, 1975, and they may all be prepared following methodologies which are known per se. Depending on the nature of B in said intermediates (II) the following procedures may be utilized for preparing them.

Intermediates of the formula (II-a)

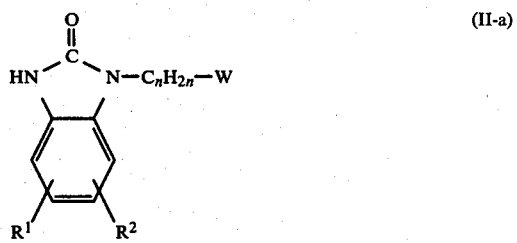

may be prepared as follows:

An appropriately substituted 2-chloronitrobenzene of formula (XVIII) is reacted with an appropriate aminoalkanol (XIX) by refluxing the reactants together in an appropriate reaction-inert organic solvent such as, for example, a lower alkanol, e.g., ethanol, propanol, 2-propanol, butanol and the like, whereupon a [(2-nitrophenyl)amino]alkanol of formula (XX) is obtained, which in turn is subjected to a nitro-to-amine reduction, e.g., by catalytic hydrogenation using Raney-nickel catalyst. The thus obtained intermediate (XXI) is then reacted with an appropriate cyclizing agent as described hereinbefore for the preparation of the compounds (I-c) starting from (IV), and the thus obtained alcohol of formula (XXII) is subsequently converted into the desired reactive ester (II-a) by the application of methodologies known in the art. Halides are conveniently prepared by the reaction of (XXII) with an appropriate halogenating agent such as, for example, sulfinyl chloride, sulfuryl chloride, phosphor pentachloride, phosphor pentabromide, phosphoryl chloride and the like. When the reactive ester is an iodide, it is preferably derived from the corresponding chloride or bromide by the replacement of that halogen with iodine. Other reactive esters such as methanesulfonates and 4-methylbenzenesulfonates are obtained by the reaction of the alcohol with an appropriate sulfonyl halide such as, for example, methanesulfonyl chloride and 4-methylbenzenesulfonyl chloride respectively.

The foregoing reactions are more clearly illustrated in the following schematic representation.

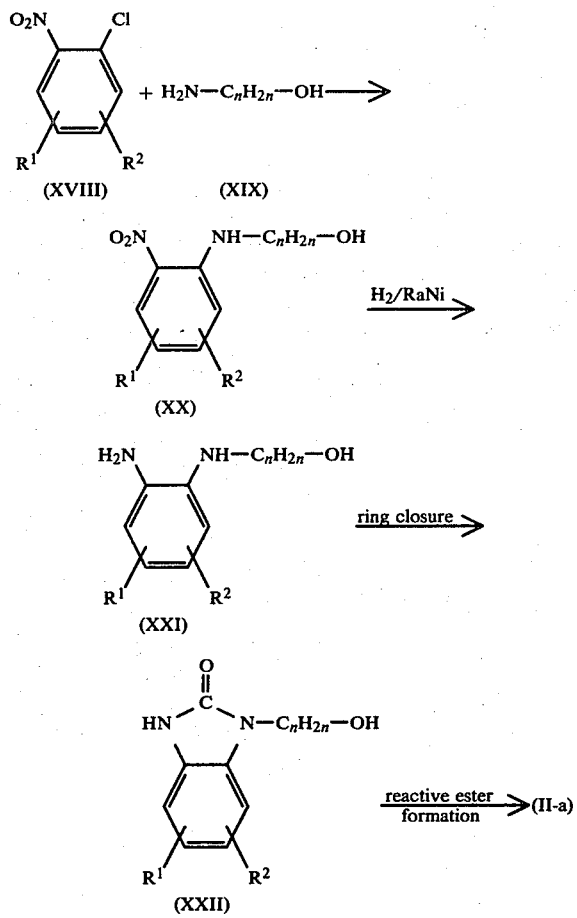

Alternatively the intermediates of formula (II-a) may also be prepared by:

(i) reacting a compound of formula (XXIII) wherein $R^3$ and $R^4$ are as previously defined with a haloalkanol of formula (XXIV) by conventional N-alkylating procedures to obtain an alcohol of formula (XXV);

(ii) converting the hydroxyl function of (XXV) into a reactive ester group in the usual manner as previously described; and (iii) eliminating the substituted ethenyl group of the thus obtained (XXVI) by acid hydrolysis as described hereinbefore for the preparation of (I-c) starting from (V).

The introduction of the hydroxyalkyl chain in (XXIII) to obtain (XXIV) may also be performed by the reaction of (XXIII) with an appropriate 2-(haloalkyloxy)tetrahydro-2H-pyran of formula (XXVII), yielding an intermediate of formula (XXVIII), the ether function of which is hydrolytically split open, e.g., by the treatment with an aqueous hydrochloric acid solution.

When the reactive ester (II-a) is a halide, (II-a-1), it may alternatively be prepared by the reaction of (XXIII) with an equivalent amount of an appropriate dihaloalkane, (XXIX) in the presence of an appropriate strong base such as, for example, sodium methoxide, or following a Mackosza procedure using aqueous alkali and a quaternary ammonium catalyst, e.g., N,N,N-triethylbenzenemethanaminium chloride, yielding an intermediate of formula (XXVI-a), the substituted ethenyl group of which is subsequently removed by acid hydrolysis, to yield the desired halide (II-a-1).

It is to be noted that the same procedures are also applicable when the substituted ethenyl group is replaced by another appropriate protecting group, except that removal thereof has to be performed following appropriate methods for the elimination of the particular group involved.

The foregoing reactions are more clearly illustrated in the following schematic representation.

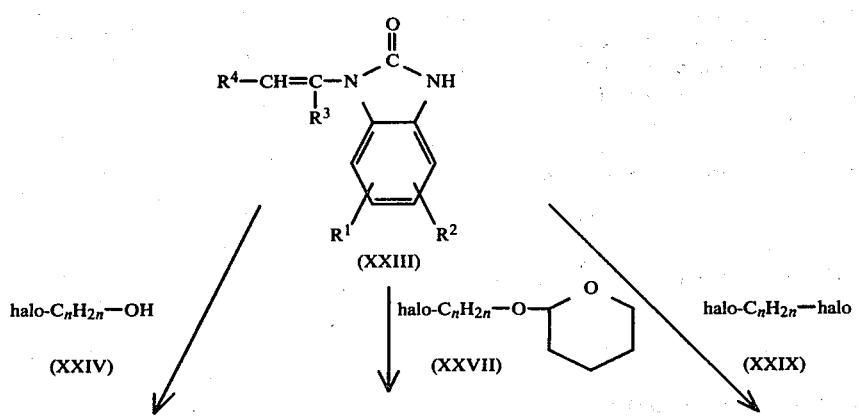

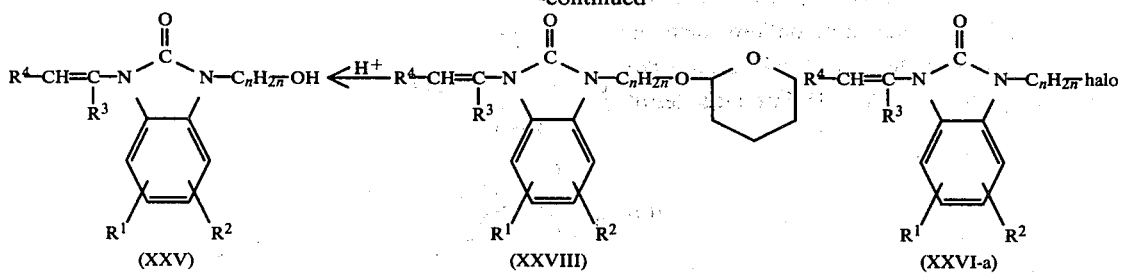

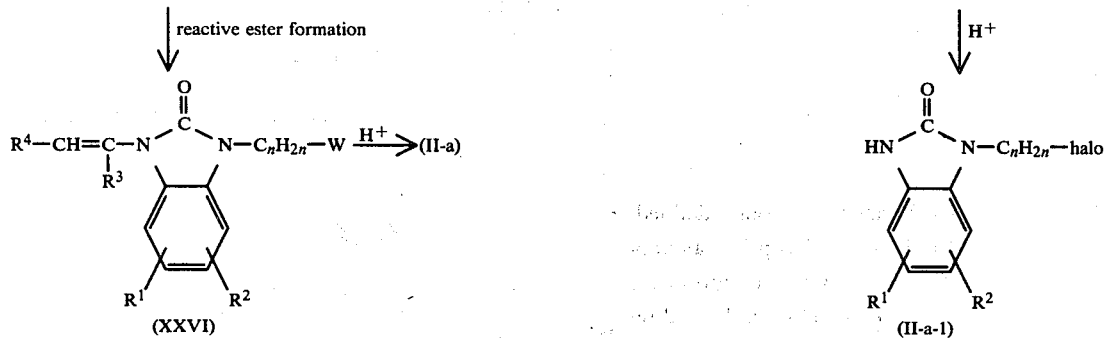

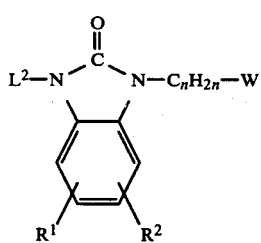

Intermediates of the formula (II-b)

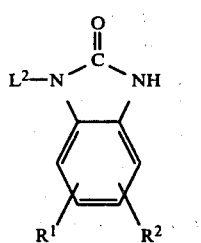

wherein $R^1$, $R^2$, n and W are as previously defined and $L^2$ is selected from the group consisting of lower alkyl, lower alkenyl, lower alkyloxycarbonyl-lower alkyl, phenyl, phenylmethyl and lower alkylaminocarbonyl, may conveniently be prepared by the introduction of the reactive ester side chain into a starting material of the formula (XXX)

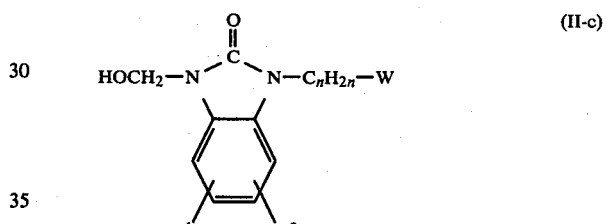

following similar procedures to those described hereinbefore for the preparation of the intermediates (XXVI) starting from (XXIII).

Intermediates of the formula (II-c)

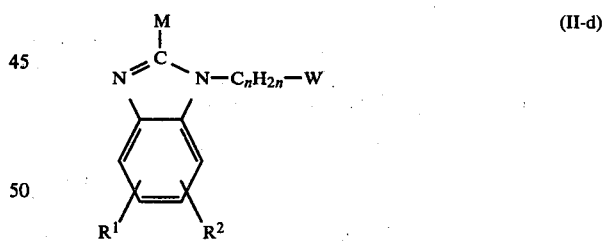

may be prepared starting from the corresponding (II-a) by hydroxymethylation of the latter in the usual manner with formaldehyde.

Intermediates of the formula (II-d)

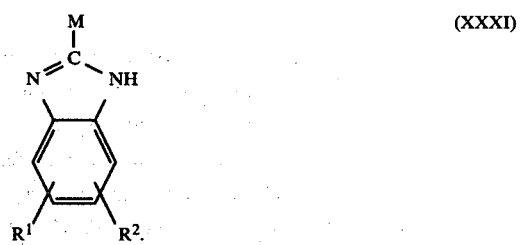

except those wherein M stands for a mercapto or lower alkylthio group, are conveniently obtained by the introduction of the reactive ester side chain into a starting material of the formula (XXXI)

The introduction of the $C_nH_{2n}$-W group may be performed following similar procedures to those described hereinbefore for the introduction of said group into starting materials of formula (XXIII). Intermediates of formula (II-e)

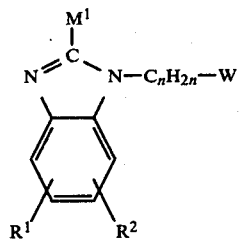
(II-e)

wherein $R^1$, $R^2$, $M^1$, n and W are as previously defined, may be prepared by subjecting an appropriate alcohol of formula (XXI) to ring closure with an appropriate cyclizing agent as described hereinbefore, followed by the conversion of the hydroxyl group of the thus obtained intermediate of formula (XXXII) into a reactive ester group.

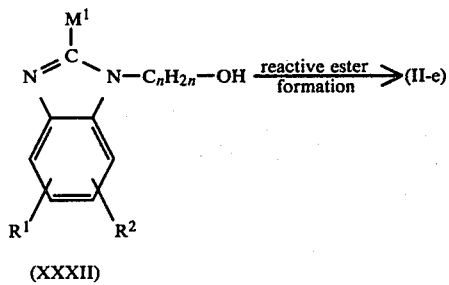
(XXXII)

The intermediates of the formula (II-f)

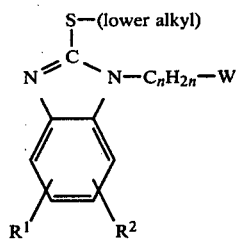
(II-f)

are conveniently obtained by S-alkylation of an appropriate intermediate of formula (XXXII), wherein $M^1$ stands for mercapto (XXXII-a), following standard S-alkylating procedures, e.g. with an appropriate halo-lower alkane and subsequent conversion of the hydroxyl function of the thus obtained (XXXIII) into a reactive ester group.

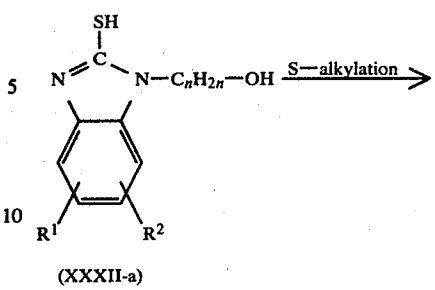
(XXXII-a)

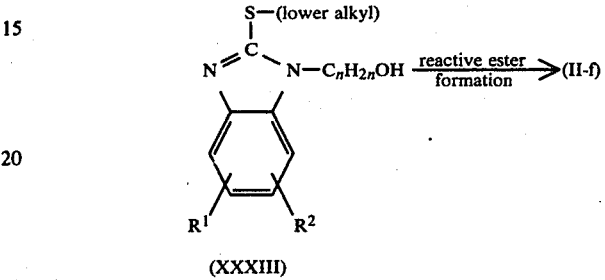
(XXXIII)

Intermediates of the formula (II-g)

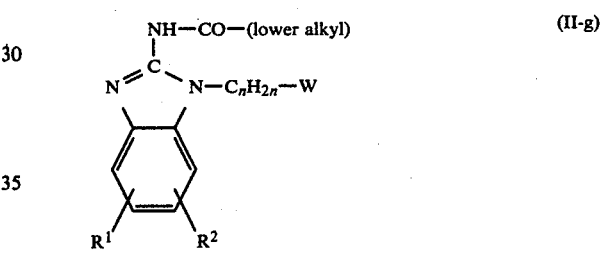
(II-g)

are conveniently prepared by N-acylation of the corresponding amino substituted analog, (II-h),

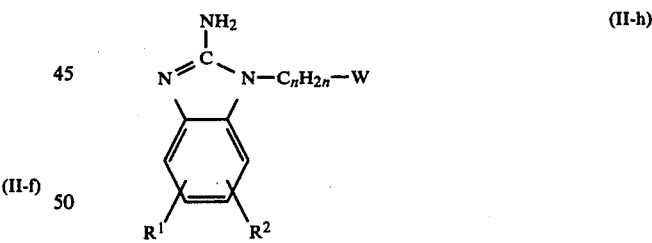
(II-h)

following procedures known to those skilled in the art, e.g., by the reaction of (II-h) with an appropriate lower alkylcarbonyl halide or with an anhydride derived from an appropriate lower alkylcarboxylic acid.

The intermediates of formula (IV) are obtained by the condensation of an appropriate reactive ester of formula (XXXIV) with a piperazine or piperidine derivative of formula (III) followed by the reduction of the nitro group of the thus obtained intermediate (XXXV) to an amino group according to standard nitro-to-amine reduction procedures, e.g., by the reaction of the nitro compound with nascent hydrogen or by catalytic hydrogenation in the presence of an appropriate catalyst such as, for example, Raney-nickel.

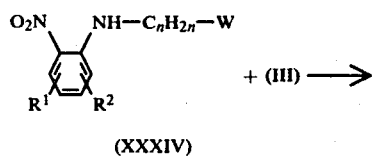

(XXXIV)

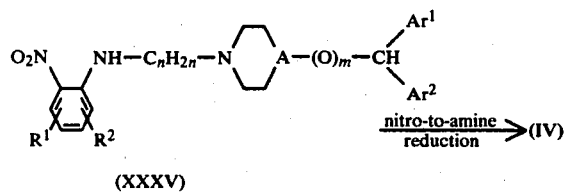

(XXXV)

The reactive esters of formula (XXXIV), used as starting materials herein are easily prepared from an alcohol of formula (XX) by the conversion of the hydroxyl function thereof into a reactive ester group following standard procedures as previously described herein.

The intermediates of formula (V) may be obtained by the condensation of a reactive ester of formula (XXXVI) with a piperazine or piperidine derivative of formula (III)

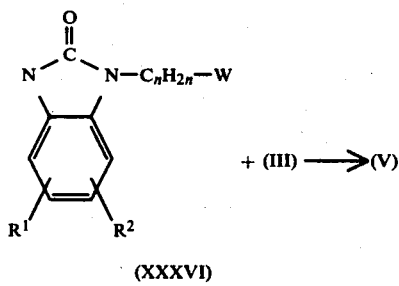

(XXXVI)

The reactive ester (XXXVI) used as a starting material herein is in turn prepared by introducing the $C_nH_{2n}W$ group into a starting material of formula (XXXVII)

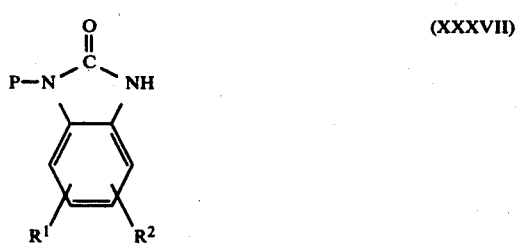

(XXXVII)

following the procedures described hereinbefore.

The intermediates of formula (XVI) may be prepared by the reaction of a reactive of formula (II) with a piperazine derivative of formula (XXXVIII) wherein Q is an appropriate protecting group such as, for example, phenylmethyl or lower alkyloxycarbonyl, and subsequently eliminating said protecting group Q from the thus obtained intermediate (XXXIX) following standard procedures as known in the art, for example, by catalytic hydrogenation using palladium-on-charcoal catalyst when Q stands for phenylmethyl, or by alkaline hydrolysis when Q stands for lower alkyloxycarbonyl.

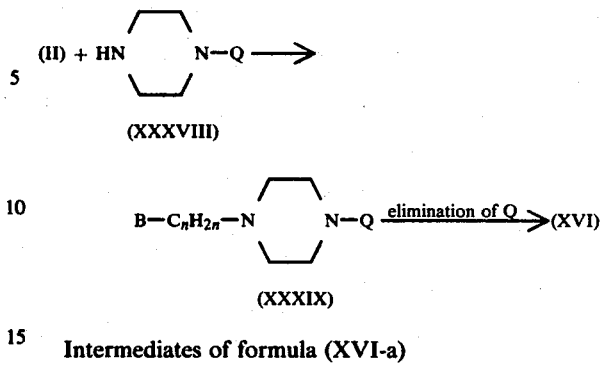

(XXXVIII)

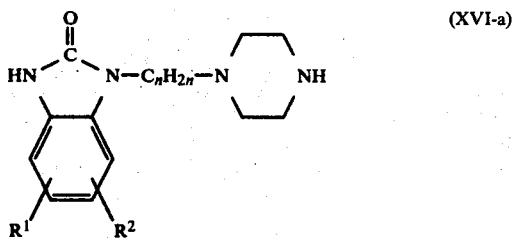

(XXXIX)

Intermediates of formula (XVI-a)

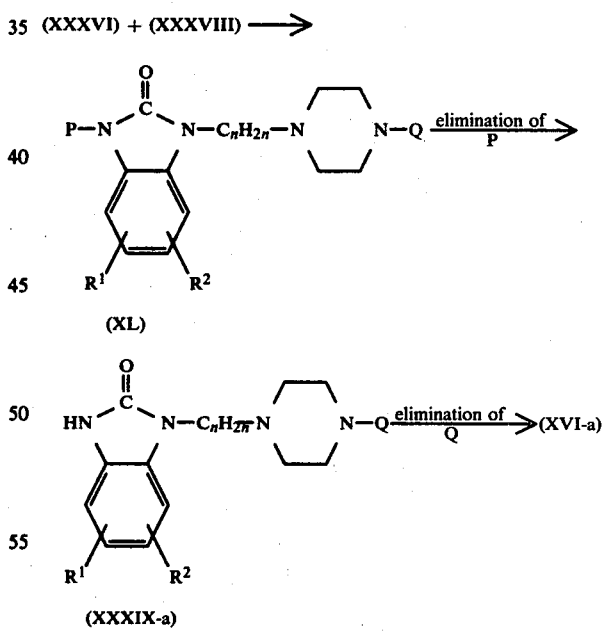

(XVI-a)

may alternatively be prepared by the reaction of (XXXVI) with (XXXVIII) to obtain an intermediate of formula (XL) and subsequently eliminating the protecting groups P and Q by appropriate procedures as generally known in the art.

(XXXVI) + (XXXVIII) ⟶

(XL)

(XXXIX-a)

Intermediates of formula (III) wherein A is

and m is 0, (III-a), are generally known and they may all be prepared by the application of methodologies known in the art. Such intermediates (III-a) may for example, be prepared by first subjecting an appropriate aroyl halide to a Friedel-Crafts reaction with an appropriate arene to obtain an $Ar^1$, $Ar^2$-methanone which in turn is reduced in the usual manner, e.g., with sodium borohydride to the corresponding methanol. The latter is then converted into a reactive ester (XVII) following standard procedures of preparing reactive esters starting from alcohols and the desired intermediates (III-a) are subsequently obtained by the reaction of (XVII) with piperazine.

The intermediates of formula (III) wherein A is

and m is 1, (III-b), may conveniently be prepared by O-alkylation of a 4-piperidinol of formula (XLI) wherein Q is an appropriate protecting group as previously defined with an appropriate reactive ester of formula (XVII), followed by the removal of the protecting group of the thus obtained (XLII) in the usual manner.

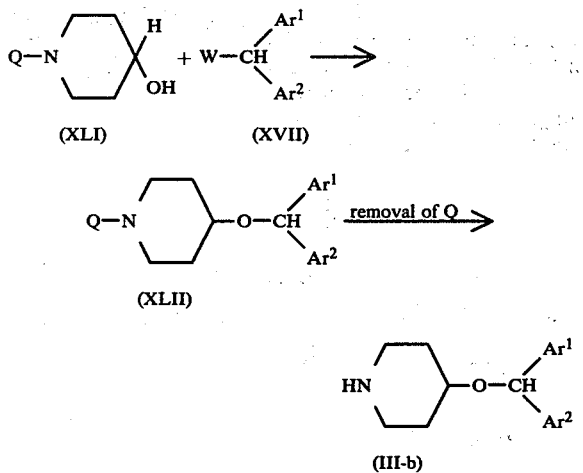

The primary starting materials used in all of the foregoing preparations are generally known and they may all be prepared following methodologies known to those skilled in the art.

The compounds of formula (I) may be converted to the therapeutically active non-toxic acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely, the salt form can be converted by treatment with alkali into the free base form.

The subject compounds of formula (I) and the pharmaceutically acceptable acid addition salts thereof possess strong anti-anaphylactic and antihistaminic properties and as such they are useful agents in human and animal therapy. The useful anti-anaphylactic and antihistaminic properties of the compounds of this invention are clearly demonstrated by the results obtained in the test procedures described hereafter.

It is emphasized that the compounds listed in the accompanying tables are not given for the purpose of limiting the invention thereto, but only to exemplify the useful anti-anaphylactic and antihistaminic properties of all the compounds within the scope of formula (I).

A. Materials and methods (a) Anti-anaphylactic and antihistaminic effects in "vivo"

The anti-anaphylactic and antihistaminic effects of the subject compounds (I) and salts thereof are studied "in vivo" in guinea pigs.

Guinea pigs, weighing between 400 and 500 g, are sensitized to ovalbumin by subplantar (s.p.) injection of 0.05 ml of antiserum in the left hind paw. The animals are then starved and orally treated, 24 hours after the sensitization, with saline (=control animals) or a particular dose of the compound under investigation.

The histamine injection (at a dose of 50 μg) was given s.p. in the right hind paw 2 hours after the oral pretreatment with the compound. The diameters of both hind paws are first measured before the histamine injection is given and again 10 minutes thereafter. The animals are challenged intravenously with 0.6 mg of ovalbumin 30 minutes after the histamine injection. All control animals develop tyical primary anaphylactic shock symptoms (coughing, difficult breathing, convulsions) and 85% of these control animals die within 15 minutes after the ovalbumin injection. Protection against death is used as the criterion for possible drug effects and the estimated $ED_{50}$-value, i.e. the oral dose whereby the protection is observed in 50% of the guinea pigs, is listed in the tables below.

The median histamine paw oe dema in 200 control animals 10 minutes after the histamine injection is 15 units (1 unit=0.1 mm). Reactions below 10 units, occurring in less than 5% of the control animals are defined as effective inhibition of histamine oe dema in the compound-treated animals and the oral dose-levels whereby this effective inhibition is seen, is also listed in the following tables.

(b) Anti-histamine activity in "vitro"

Guinea-pig ileum strips are suspended in a 100 ml Tyrode bath at 37.5° C. with a preload of 0.75 g and gassed with 95% $O_2$ and 5% $CO_2$.

The histamine-(0.5 mg/liter) induced spasms are recorded Kymographically with an isotonic lever giving a 5-fold magnification. The interaction of the compound to be tested (5 minutes incubation time) with the agonist is studied and the tables below give the effective concentration (in mg/l) of the different compounds whereby a significant inhibition (50%) of the histamine-induced contraction is measured.

As a result of the foregoing tests, the subject compounds (I) and pharmaceutically acceptable salts thereof are generally found active as anti-allergic agents in doses ranging from about 0.25 to about 20 mg/kg body weight upon systemic administration to warm-blooded animals.

In view of their useful antihistaminic and anti-anaphylactic activity, the subject compounds may be formulated into various pharmaceutical forms for administration purposes. To prepare the pharmaceutical compositions of this invention, an effective antihistaminic or anti-anaphylactic amount of the particular compound, in base or acid-addition salt form, as the active ingredient is combined in intimate admixture with a pharmaceutically acceptable carrier, which carrier may take a wide variety of forms depending on the form of preparation desired for administration.

These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like; and segregated multiples thereof.

TABLE I-a

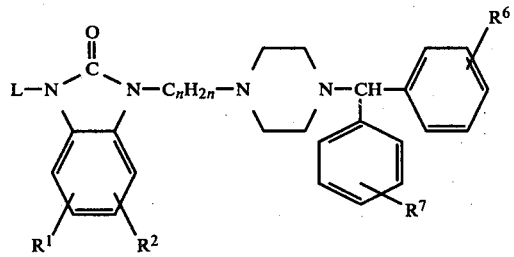

| L | $R^1$ | $R^2$ | $C_nH_{2n}$ | $R^6$ | $R^7$ | Base or Salt form | Histamine in "vitro" (ileum) effective conc. in mg/l | Anaphylaxis in guinea pigs oral effective dose in mg/kg | |
|---|---|---|---|---|---|---|---|---|---|
| | | | | | | | | Survival | Histamine oedema |
| H | H | H | $(CH_2)_2$ | H | H | base | 0.01 | 0.63 | 1.25 |
| H | 5-Cl | H | $(CH_2)_2$ | H | H | base | 0.01 | 0.63 | 1.25 |
| H | H | 6-Cl | $(CH_2)_2$ | H | H | base | 0.02 | 2.5 | 2.5 |
| H | 5-CF$_3$ | H | $(CH_2)_2$ | H | H | base | 0.02 | 0.31 | 1.25 |
| H | 5-CH$_3$ | H | $(CH_2)_2$ | H | H | base | 0.01 | 1.25 | 1.25 |
| H | H | H | $(CH_2)_2$ | 4-F | H | base | 0.02 | 0.31 | 0.16 |
| H | H | H | $(CH_2)_2$ | 4-F | 4-F | base ½H$_2$O | 0.02 | 0.63 | 0.63 |
| H | H | H | $(CH_2)_3$ | H | H | base | 0.005 | 0.10 | 0.31 |
| H | 5-Cl | H | $(CH_2)_3$ | H | H | base | 0.01 | 0.63 | 1.25 |
| H | 5-CH$_3$ | H | $(CH_2)_3$ | H | H | base | 0.01 | 0.08 | 0.16 |
| H | H | 6-Cl | $(CH_2)_3$ | H | H | base | 0.04 | 0.63 | 0.63 |
| H | H | 6-CH$_3$ | $(CH_2)_3$ | H | H | base | 0.01 | 0.16 | 0.31 |
| H | H | 7-Cl | $(CH_2)_3$ | H | H | base | 0.08 | ≧2.5 | — |
| H | 5-Cl | 6-Cl | $(CH_2)_3$ | H | H | base | ≧0.16 | 2.5 | 2.5 |
| H | 5-CF$_3$ | H | $(CH_2)_3$ | H | H | base | 0.02 | 0.31 | 0.31 |
| CH$_2$=C(CH$_3$)— | H | H | $(CH_2)_3$ | H | H | base | 0.01 | 0.16 | 0.31 |
| C$_2$H$_5$—OOC—(CH$_2$)$_2$ | H | H | $(CH_2)_3$ | H | H | 2HCl.2H$_2$O | 0.005 | 0.63 | 0.63 |
| C$_6$H$_5$—CH$_2$— | H | H | $(CH_2)_3$ | H | H | 2HCl | 0.16 | 1.25 | 1.25 |
| CH$_3$—CO— | H | H | $(CH_2)_3$ | H | H | base | 0.005 | 0.10 | 0.31 |
| CH$_3$—NH—CO— | H | H | $(CH_2)_3$ | H | H | base | 0.02 | — | — |
| CH$_3$— | H | H | $(CH_2)_3$ | H | H | 2HCl.H$_2$O | 0.01 | 1.25 | 2.5 |
| HOCH$_2$— | H | H | $(CH_2)_3$ | H | H | base | 0.01 | 0.31 | 0.31 |
| C$_6$H$_5$— | 5-Cl | H | $(CH_2)_3$ | H | H | 2HCl.½H$_2$O | 0.08 | — | — |
| H | H | H | $(CH_2)_3$ | 4-F | H | base | 0.01 | 0.31 | 0.31 |
| H | H | H | $(CH_2)_3$ | 4-Cl | H | base | 0.01 | 1.25 | 0.63 |
| H | H | H | $(CH_2)_3$ | 3-Cl | H | base | 0.01 | 0.63 | 1.25 |

TABLE I-a-continued

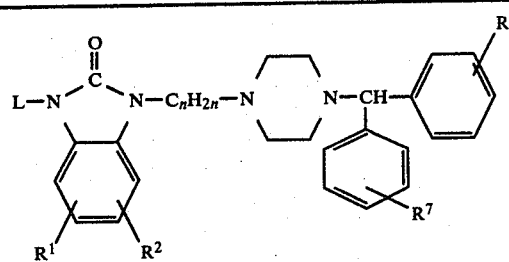

| L | R¹ | R² | $C_nH_{2n}$ | R⁶ | R⁷ | Base or Salt form | Histamine in "vitro" (ileum) effective conc. in mg/l | Anaphylaxis in guinea pigs oral effective dose in mg/kg Survival | Histamine oedema |
|---|---|---|---|---|---|---|---|---|---|
| H | H | H | (CH₂)₃ | 4-F | 4-F | base | 0.01 | 0.31 | 0.16 |
| H | 5-Cl | H | (CH₂)₃ | 4-F | 4-F | base | 0.04 | 1.25 | 1.25 |
| H | H | 6-Cl | (CH₂)₃ | 4-F | 4-F | base.H₂O | 0.02 | 0.63 | 1.25 |
| H | H | H | (CH₂)₃ | 2-F | 4-Cl | base | 0.02 | 0.31 | 1.25 |
| H | H | H | (CH₂)₄ | H | H | base | 0.01 | 0.16 | 0.31 |
| H | H | H | (CH₂)₄ | 4-F | 4-F | 2HCl.H₂O ½C₂H₅OH | 0.01 | 0.16 | 0.31 |
| H | H | H | (CH₂)₅ | H | H | 2HCl.H₂O | 0.01 | 0.63 | 2.5 |
| H | H | H | (CH₂)₅ | 4-F | 4-F | 2HCl.H₂O | 0.01 | 1.25 | 2.5 |
| H | H | H | (CH₂)₆ | H | H | base | 0.01 | 1.25 | 2.5 |
| H | H | H | —CH₂—CH(CH₃)—CH₂— | 4-F | 4-F | base | 0.02 | 1.25 | 1.25 |
| H | H | H | (CH₂)₃ | H | 2-Cl | base | 0.08 | — | — |
| H | H | H | (CH₂)₃ | 4-Cl | 4-Cl | base | 0.16 | <2.5 | <2.5 |
| H | H | H | (CH₂)₃ | H | 4-Br | base | 0.16 | <2.5 | <2.5 |
| H | H | H | (CH₂)₃ | H | 2-F | base | 0.02 | <2.5 | <2.5 |
| H | H | H | (CH₂)₃ | 4-F | 4-CH₃ | base | 0.16 | <2.5 | <2.5 |
| H | H | H | (CH₂)₃ | H | 4-CH₃ | base | 0.08 | <2.5 | <2.5 |
| H | H | H | (CH₂)₃ | H | 4-NO₂ | base | 0.16 | <2.5 | <2.5 |
| HOOC—CH₂ | H | H | (CH₂)₃ | H | H | base ½H₂O | 0.08 | <2.5 | <2.5 |

TABLE I-b

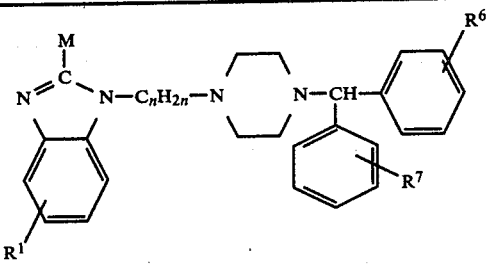

| M | R¹ | $C_nH_{2n}$ | R⁶ | R⁷ | Base or Salt form | Histamine in "vitro" (ileum) effective conc. in mg/l | Anaphylaxis in guinea pigs oral effective dose in mg/kg Survival | Histamine oedema |
|---|---|---|---|---|---|---|---|---|
| H | H | (CH₂)₂ | H | H | Base | 0.005 | 1.25 | 1.25 |
| C₂H₅— | H | (CH₂)₂ | H | H | 3HCl.H₂O | ≧0.16 | — | — |
| H | H | (CH₂)₃ | H | H | base | 0.0025 | 0.08 | 0.16 |
| CH₃—S— | H | (CH₂)₃ | H | H | 3HCl.H₂O | 0.16 | 1.25 | 1.25 |
| CH₃— | H | (CH₂)₃ | H | H | base | 0.02 | 2.5 | 2.5 |
| C₆H₅— | H | (CH₂)₃ | H | H | base | 0.08 | — | — |
| HS— | H | (CH₂)₃ | H | H | base | 0.01 | 0.63 | 1.25 |
| cyclohexyl- | H | (CH₂)₃ | H | H | base | ≧0.16 | 2.5 | 2.5 |
| C₆H₅—CH₂— | H | (CH₂)₃ | H | H | 3HCl.H₂O | ≧0.16 | — | — |
| CH₃OOC—NH— | H | (CH₂)₃ | H | H | base | ≦0.16 | 2.5 | 2.5 |
| H₂N— | H | (CH₂)₃ | H | H | base | ≦0.16 | 2.5 | 2.5 |
| CH₃—CO—NH— | H | (CH₂)₃ | H | H | base | ≧0.16 | 2.5 | — |
| C₂H₅— | H | (CH₂)₃ | H | H | 3HCl.H₂O | 0.01 | 2.5 | 2.5 |
| cyclohexyl- | 5-Cl | (CH₂)₃ | H | H | base | — | 0.63 | 2.5 |
| C₂H₅— | 5-Cl | (CH₂)₃ | H | H | 3HCl.H₂O | 0.01 | — | — |
| C₆H₅—CH₂— | 5-Cl | (CH₂)₃ | H | H | 3HCl.H₂O | — | 2.5 | — |
| C₆H₅— | 6-Cl | (CH₂)₃ | H | H | base | — | 2.5 | — |
| cyclohexyl- | 6-Cl | (CH₂)₃ | H | H | base | — | 2.5 | — |

TABLE I-b-continued

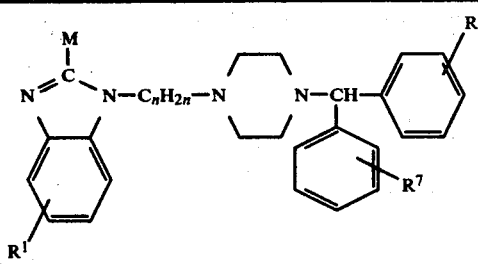

| M | R[1] | $C_nH_{2n}$ | R[6] | R[7] | Base or Salt form | Histamine in "vitro" (ileum) effective conc. in mg/l | Anaphylaxis in guinea pigs oral effective dose in mg/kg | |
|---|---|---|---|---|---|---|---|---|
| | | | | | | | Survival | Histamine oedema |
| H | H | $(CH_2)_3$ | 4-F | H | base | 0.005 | 0.31 | 0.31 |
| H | H | $(CH_2)_3$ | 2-Cl | H | 3HCl2H$_2$O | 0.01 | 1.25 | 1.25 |
| H | H | $(CH_2)_3$ | 4-Cl | H | base | 0.01 | 0.08 | 0.31 |
| H | H | $(CH_2)_3$ | 4-F | 4-F | base H$_2$O | 0.02 | 0.16 | 0.31 |
| H | H | $(CH_2)_4$ | H | H | base | 0.0025 | 0.16 | 0.16 |
| CH$_3$ | H | $(CH_2)_4$ | H | H | base | 0.005 | 1.25 | 1.25 |
| H | H | $(CH_2)_4$ | 4-F | H | base | 0.005 | 0.08 | 0.16 |
| H | H | $(CH_2)_4$ | 3-Cl | H | 3HCl.H$_2$O ½CH$_3$CHOHCH$_3$ | 0.01 | 1.25 | 1.25 |
| H | H | $(CH_2)_4$ | 4-F | 4-F | base | 0.005 | 0.31 | 0.31 |
| H | H | CH$_2$—CH(CH$_3$)—CH$_2$ | H | H | 3HCl½H$_2$O | 0.02 | — | — |
| H | H | CH$_2$—CH(CH$_3$)—CH$_2$ | 4-F | 4-F | 3HCl½H$_2$O | 0.02 | 0.63 | 1.25 |

TABLE I-c

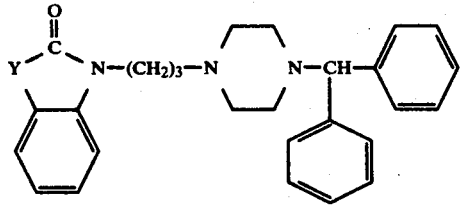

| Y | Base or Salt form | Histamine in "vitro" (ileum) effective conc. in mg/l | Anaphylaxis in guinea pigs oral effective dose in mg/kg | |
|---|---|---|---|---|
| | | | Survival | Histamine oedema |
| S | 2 HCl.½ H$_2$O | 0.01 | 1.25 | 1.25 |

TABLE I-c-continued

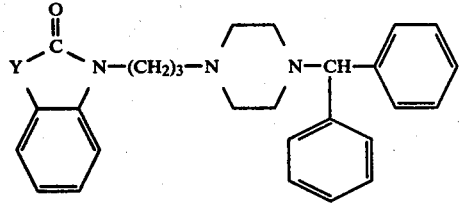

| Y | Base or Salt form | Histamine in "vitro" (ileum) effective conc. in mg/l | Anaphylaxis in guinea pigs oral effective dose in mg/kg | |
|---|---|---|---|---|
| | | | Survival | Histamine oedema |
| O | 2 HCl | 0.01 | 0.63 | 2.5 |

TABLE I-d

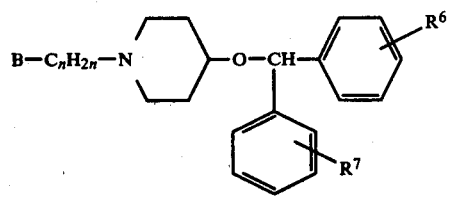

| B | $C_nH_{2n}$ | R[6] | R[7] | Base or Salt form | Histamine in "vitro" (ileum) effective dose in mg/l | Anaphylaxis in guinea pigs oral effective dose in mg/kg | |
|---|---|---|---|---|---|---|---|
| | | | | | | Survival | Histamine oedema |
| (benzimidazolinone) | $(CH_2)_2$ | H | H | HCl | 0.0025 | 0.31 | 0.16 |

TABLE I-d-continued
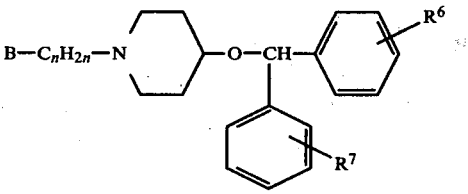
| B | $C_nH_{2n}$ | $R^6$ | $R^7$ | Base or Salt form | Histamine in "vitro" (ileum) effective dose in mg/l | Anaphylaxis in guinea pigs oral effective dose in mg/kg | |
|---|---|---|---|---|---|---|---|
| | | | | | | Survival | Histamine oedema |
| 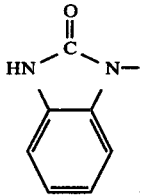 | (CH₂)₃ | H | H | base | 0.0025 | 0.63 | 1.25 |
| 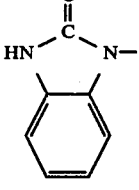 | (CH₂)₄ | H | H | base | 0.005 | 0.63 | 0.31 |
| 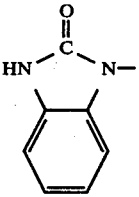 | (CH₂)₂ | 4-F | 4-F | HCl.½ H₂O | 0.0025 | 0.31 | 0.31 |
| 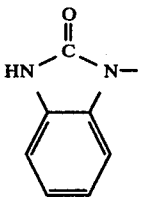 | (CH₂)₃ | 4-F | 4-F | HCl.½ H₂O | 0.0025 | 0.63 | 0.63 |
| 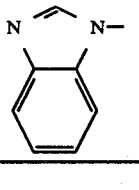 | (CH₂)₃ | H | H | base | 0.0025 | 0.16 | 0.16 |

TABLE I-e

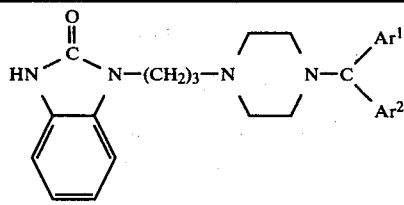

| Ar[1] | Ar[2] | Base or Salt Form | Histamine in "vitro" (ileum) effective dose in mg/l | Anaphylaxis in guinea pigs oral effective dose in mg/kg | |
|---|---|---|---|---|---|
| | | | | Survival | Histamine oedema |
| $C_6H_5$ | 2-pyridinyl | base | 0.16 | — | 2.5 |
| $C_6H_5$ | 3-pyridinyl | base | 0.08 | — | <2.5 |
| $C_6H_5$ | 2,5-$(CH_3)_2$—$C_6H_3$ | base | 0.16 | — | — |
| 4-Cl—$C_6H_4$ | 3-pyridinyl | base | 0.08 | 1.25 | 2.5 |
| 4-F—$C_6H_4$ | 3-pyridinyl | base | 0.08 | <2.5 | <2.5 |
| 4-F—$C_6H_4$ | 4-pyridinyl | base | 0.16 | — | ≦2.5 |

The following examples are intended to illustrate but not to limit the scope of the present invention. Unless otherwise stated all parts therein are by weight.

EXAMPLE I

To a stirred and hot mixture of 54 parts of 1,3-dihydro-1-(phenylmethyl)-2H-benzimidazol-2-one, 47.25 parts of 1-bromo-3-chloropropane and 6 parts of N,N,N-triethylbenzenemethanaminium chloride are added dropwise 450 parts of a sodium hydroxide solution 60% at 60° C. Upon completion, stirring is continued for 6 hours at 60° C. The reaction mixture is cooled and poured onto water. The oily product is extracted with trichloromethane. The extract is dried, filtered and evaporated. The residue is crystallized from 2,2'-oxybispropane, yielding, after drying, 1-(3-chloropropyl)-1,3-dihydro-3-(phenylmethyl)-2H-benzimidazol-2-one.

EXAMPLE II

To a stirred and hot (50° C.) mixture of 47 parts of 1,3-dihydro-6-methyl-1-(1-methylethyl)-2H-benzimidazol-2-one and 5 parts of N,N,N-triethylbenzenemethanaminium chloride in 300 parts of a sodium hydroxide solution 50% are added 79 parts of 1-bromo-3-chloropropane. The whole is heated to 60° C.: exothermic reaction (temperature rises to 75° C.). Stirring is continued for one hour while cooling to keep the temperature between 60° and 70° C. The reaction mixture is cooled and poured onto crushed ice. The product is extracted with methylbenzene. The extract is washed three times with water, dried, filtered and evaporated. The oily residue is distilled, yielding 1-(3-chloropropyl)-1,3-dihydro-5-methyl-3-(1-methylethyl)-2H-benzimidazol-2-one; bp. 140° C. at 0.015 mm. pressure.

EXAMPLE III

To a stirred and hot (±50° C.) mixture of 34 parts of 1,3-dihydro-5-methyl-1-(1-methylethyl)-2H-benzimidazol-2-one, 5 parts of N,N,N-triethylbenzenemethanaminium chloride and 300 parts of a sodium hydroxide solution 50% are added 57 parts of 1-bromo-3-chloropropane (exothermic reaction: temperature rises to 70° C.). The whole is stirred for one hour at 65°-70° C. The reaction mixture is cooled and poured onto crushed ice. The product is extracted with methylbenzene. The extract is washed three times with water, dried, filtered and evaporated. The oily residue is distilled, yielding 3-(3-chloropropyl)-1,3-dihydro-5-methyl-1-(1-methylethyl)-2H-benzimidazol-2-one; bp. 140° C. at 0.02 mm. pressure.

EXAMPLE IV

To a stirred solution of 7 parts of 6-chloro-1,3-dihydro-1-phenyl-2H-benzimidazol-2-one in 67.5 parts of N,N-dimethylformamide is added portionwise 1 part of a sodium hydride dispersion 78%. After stirring for 2 hours at room temperature, there are added dropwise (slowly) 4.75 parts of 1-bromo-3-chloropropane. Upon completion, stirring is continued first for two hours at room temperature and further for one hour at 60° C. The reaction mixture is poured onto water and the product is extracted with methylbenzene. The extract is dried, filtered and evaporated. The residue is purified by column-chromatography over silica gel using a mixture of trichloromethane and 5% of methanol as eluent. The pure fractions are collected and the eluent is evaporated, yielding 5-chloro-1-(3-chloropropyl)-1,3-dihydro-3-phenyl-2H-benzimidazol-2-one as a residue.

EXAMPLE V

To a stirred and hot (50° C.) mixture of 28.3 parts of 1,3-dihydro-1-(1-methylethyl)-2H-benzimidazol-2-one, 5 parts of N,N,N-triethylbenzenemethanaminium chloride and 225 parts of a sodium hydroxide solution 60% are added dropwise, during a 30 minutes-period, 33.7 parts of 1-bromo-4-chlorobutane. Upon completion, stirring is continued for 5 hours at 60° C. The reaction mixture is cooled, water is added and the product is extracted with methylbenzene. The extract is dried, filtered and evaporated, yielding 1-(4-chlorobutyl)-1,3-dihydro-3-(1-methylethyl)-2H-benzimidazol-2-one as a residue.

EXAMPLE VI

To a stirred suspension of 3.2 parts of a sodium hydride dispersion 70% in 9 parts of N,N-dimethylformamide is added dropwise, during a 2 hours-period, a mixture of 17.4 parts of 1,3-dihydro-1-(1-methylethyl)-2H-benzimidazol-2-one, 70.5 parts of 1,5-dichloropentane and 45 parts of N,N-dimethylformamide at 25°-30° C. Upon completion, stirring is continued for 2 hours at room temperature. The reaction mixture is filtered over hyflo and the filtrate is evaporated. The residue is taken up in 90 parts of methylbenzene and the whole is stirred with activated charcoal. The latter is filtered off. The filtrate is washed with water, dried, filtered and evaporated in an oil-bath at 120° C. (water-jet), yielding 1-(5-chloropentyl)-1,3-dihydro-3-(1-methylethenyl)-2H-benzimidazol-2-one as a residue.

EXAMPLE VII

To a stirred mixture of 3.2 parts of a sodium hydride dispersion 70% in 9 parts of N,N-dimethylformamide is added dropwise (slowly), during a 2 hours-period, a mixture of 17.4 parts of 1,3-dihydro-1-(1-methylethenyl)-2H-benzimidazol-2-one, 77.5 parts of 1,6-dichlorohexane and 36 parts of N,N-dimethylformamide. Upon completion, stirring is continued overnight at room temperature. The reaction mixture is filtered over hyflo and the N,N-dimethylformamide is evaporated in vacuo. The excess of 1,6-dichlorohexane is distilled off in an oil-bath with water-jet. The residue is dissolved in methylbenzene and the solution is stirred with activated charcoal. The latter is filtered off over hyflo and the filtrate is evaporated, yielding 1-(6-chlorohexyl)-1,3-dihydro-3-(1-methylethenyl)-2H-benzimidazol-2-one as an oily residue.

EXAMPLE VIII

To a stirred mixture of 5 parts of 4-chloro-1,3-dihydro-3-(3-hydroxypropyl)-2H-benzimidazol-2-one and 75 parts of trichloromethane are added dropwise 8 parts of sulfinyl chloride. Upon completion, stirring is continued for 3 hours at reflux temperature. The reaction mixture is cooled and evaporated. The residue is stirred in a small amount of 4-methyl-2-pentanone. The product is filtered off and dried, yielding 4-chloro-3-(3-chloropropyl)-1,3-dihydro-2H-benzimidazol-2-one.

EXAMPLE IX

To a stirred mixture of 13.2 parts of 2-methyl-1H-benzimidazole, 2 parts of N,N,N-triethylbenzenemethanaminium chloride and 150 parts of a sodium hydroxide solution 60% are added 30 parts of 1-bromo-3-chloropropane. To start the reaction, the whole is heated to about 40° C., whereupon the temperature rises to 50° C. (exothermic reaction). Stirring at about 50° C. is continued for 30 minutes. The reaction mixture is poured onto water and the product is extracted with methylbenzene. The extract is dried, filtered and evaporated. The residue is purified by column-chromatography over silica gel using a mixture of trichloromethane and methanol (90:10) as eluent. The pure fractions are collected and the eluent is evaporated, yielding 1-(3-chloropropyl)-2-methyl-1H-benzimidazole as a residue.

EXAMPLE X

A mixture of 20 parts of 2-cyclohexyl-1H-benzimidazole, 2 parts of N,N,N-triethylbenzenemethanaminium chloride, 225 parts of a sodium hydroxide solution 50% and 140 parts of tetrahydrofuran is stirred and heated to 40° C. Then there are added 31.5 parts of 1-bromo-3-chloropropane and stirring is continued for 15 minutes at 60° C. The reaction mixture is cooled, methylbenzene is added and the layers are separated. The aqueous phase is extracted with methylbenzene. The combined methylbenzene-phases are washed with water, dried, filtered and evaporated. The residue is purified by column-chromatography over silica gel using a mixture of trichloromethane and methanol (95:5) as eluent. The pure fractions are collected and the eluent is evaporated, yielding 1-(3-chloropropyl)-2-cyclohexyl-1H-benzimidazole as an oily residue.

EXAMPLE XI

To a stirred mixture of 29.2 parts of 2-ethyl-1H-benzimidazole, 5 parts of N,N,N-triethylbenzenemethanaminium chloride and 300 parts of a sodium hydroxide solution 60% are added 60 parts of 1-bromo-3-chloropropane. The whole is heated to about 65° C. and stirring is continued for 30 minutes at this temperature. Methylbenzene is added and the whole is poured onto water. The organic phase is separated, dried, filtered and evaporated. The residue is purified twice by column-chromatography over silica gel using a mixture of trichloromethane and methanol (90:10) as eluent. The pure fractions are collected and the eluent is evaporated, yielding 1-(3-chloropropyl)-2-ethyl-1H-benzimidazole as a residue.

EXAMPLE XII

To a stirred and warm (40° C.) mixture of 9.5 parts of 1H-benzimidazole, 2 parts of N,N,N-triethylbenzenemethanaminium chloride, 225 parts of a sodium hydroxide solution 50% and 90 parts of tetrahydrofuran are added 17 parts of 1-bromo-3-chloro-2-methylpropane. The whole is heated to about 60° C. and stirring is continued for 15 minutes at this temperature. The reaction mixture is cooled and the product is extracted with trichloromethane. The extract is dried, filtered and evaporated. The oily residue is purified by column-chromatography over silica gel using a mixture of trichloromethane and methanol (95:5) as eluent. The pure fractions are collected and the eluent is evaporated, yielding 1-(3-chloro-2-methylpropyl)-1H-benzimidazole as an oily residue.

EXAMPLE XIII

A mixture of 38.8 parts of 2-phenyl-1H-benzimidazole, 44 parts of a sodium methoxide solution 30% and 320 parts of 2-propanol is stirred and heated for 15 minutes at 50° C. After cooling, there are added 47.25 parts of 1-bromo-3-chloropropane. The whole is stirred and refluxed for 3 hours. The reaction mixture is evaporated. The residue is diluted with water and the product is extracted with methylbenzene. The extract is dried, filtered and evaporated, yielding 1-(3-chloropropyl)-2-phenyl-1H-benzimidazole as a residue.

EXAMPLE XIV

To a stirred mixture of 13.2 parts of 2-methyl-1H-benzimidazole, 3 parts of N,N,N-triethylbenzenemethanaminium chloride and 225 parts of a sodium hydroxide solution 60% are added 25 parts of 1,4-dichlorobutane. The whole is heated to about 100° C. and stirring is continued for one hour at this temperature. The reaction mixture is cooled and poured onto ice-water. The product is extracted with methylbenzene. The extract is dried, filtered and evaporated. The residue is purified by column-chromatography over silica gel using a mixture of trichloromethane and methanol (90:10) as eluent. The pure fractions are collected and eluent is evaporated, yielding 1-(4-chlorobutyl)-2-methyl-1H-benzimidazole as a residue.

EXAMPLE XV

To a stirred mixture of 45 parts of 5-chloro-2(phenylmethyl)-1H-benzimidazole-1-propanol and 225 parts of trichloromethane are added dropwise 29.75 parts of sulfinyl chloride. Upon completion, stirring is continued for 6 hours at reflux temperature. The reaction mixture is evaporated and the residue is taken up in water. The product is extracted with trichloromethane. The extract is dried, filtered and evaporated. The residue is purified by column-chromatography over silica gel using a mixture of trichloromethane and methanol (98:2) as eluent. The pure fractions are collected and the eluent is evaporated, yielding 5-chloro-1-(3-chloropropyl)-2-(phenylmethyl)-1H-benzimidazole as a solid residue.

EXAMPLE XVI

A mixture of 20 parts of 3-[(2-amino-4-chlorophenyl)amino]-1-propanol, 50 parts of acetic acid and 150 parts of a hydrochloric acid solution 4 N is stirred and refluxed overnight. The reaction mixture is cooled and evaporated. The residue is dissolved in water and the solution is alkalized with ammonium hydroxide. The product is extracted with trichloromethane. The extract is dried, filtered and evaporated. The residue is crystallized from a mixture of 4-methyl-2-pentanone and 2,2'-oxybispropane, yielding 5-chloro-2-methyl-1H-benzimidazole-1-propanol.

To a stirred mixture of 6.5 parts of 5-chloro-2-methyl-1H-benzimidazole-1-propanol and 120 parts of trichloromethane are added dropwise 12 parts of sulfinyl chloride. Upon completion, the whole is heated to reflux and stirring is continued for 3 hours at reflux temperature. The reaction mixture is cooled and evaporated. Water is added to the residue and the mixture is treated with activated charcoal. The latter is filtered off and the filtrate is alkalized with ammonium hydroxide. The product is extracted with trichloromethane. The extract is dried, filtered and evaporated. The residue is crystallized from 2,2'-oxybispropane. The product is filtered off and dried, yielding 5-chloro-1-(3-chloropropyl)-2-methyl-1H-benzimidazole.

EXAMPLE XVII

A mixture of 30 parts of 3-[(2-amino-4-chlorophenyl)amino]-1-propanol, 20 parts of propanoic acid and 200 parts of a hydrochloric acid solution 4 N is stirred and refluxed for 3 hours. The reaction mixture is cooled, water and crushed ice are added and the whole is treated with activated charcoal. The latter is filtered off and the filtrate is alkalized with ammonium hydroxide. The product is extracted with methylbenzene. The extract is dried, filtered and evaporated. The residue is crystallized from 4-methyl-2-pentanone. The product is filtered off and dried, yielding 5-chloro-2-ethyl-1H-benzimidazole-1-propanol.

To a stirred mixture of 4 parts of 5-chloro-2-ethyl-1H-benzimidazole-1-propanol and 150 parts of trichloromethane are added dropwise 9.6 parts of sulfinyl chloride. Upon completion, the whole is heated to reflux and stirring is continued for 2 hours at reflux temperature. The reaction mixture is cooled and evaporated. The residue is taken up in water and stirred with activated charcoal. The latter is filtered off and the filtrate is alkalized with ammonium hydroxide. The product is extracted with trichloromethane. The extract is dried, filtered and evaporated, yielding 5-chloro-1-(3-chloropropyl)-2-ethyl-1H-benzimidazole.

EXAMPLE XVIII

To a stirred and refluxing (water-separator) mixture of 30 parts of 3-[(2-amino-4-chlorophenyl)amino]-1-propanol and 0.1 parts of 4-methylbenzenesulfonic acid in 405 parts of methylbenzene is added dropwise a solution of 34 parts of cyclohexanecarboxaldehyde in 45 parts of methylbenzene. Upon completion, stirring is continued for one hour at reflux temperature and with water-separator. The methylbenzene is removed by evaporation in vacuo and the residue is triturated in 2,2'-oxybispropane. The product is filtered off and dried, yielding 5-chloro-2-cyclohexyl-1H-benzimidazole-1-propanol; mp. 95° C.

To a stirred mixture of 21 parts of 5-chloro-2-cyclohexyl-1H-benzimidazole-1-propanol in 225 parts of trichloromethane are added dropwise 40 parts of sulfinyl chloride (exothermic reaction). Upon completion, stirring is continued for 2 hours at reflux temperature. The reaction mixture is evaporated and the residue is dissolved in boiling water. The solution is treated with activated charcoal. The latter is filtered off till a clear filtrate is obtained. After cooling in an ice-bath, the precipitated product is filtered off and dried, yielding 5-chloro-1-(3-chloropropyl)-2-cyclohexyl-1H-benzimidazole hydrochloride; mp. 211.7° C.

EXAMPLE XIX

To a stirred mixture of 40 parts of 2-(phenylmethyl)-1H-benzimidazole-1-propanol and 225 parts of trichloromethane are added dropwise 30 parts of sulfinyl chloride. Upon completion, stirring is continued for 4 hours at reflux temperature. The reaction mixture is evaporated and the residue is boiled in water. The solution is filtered over hyflo and the filtrate is alkalized with ammonium hydroxide. The product is extracted with trichloromethane. The extract is dried, filtered and evaporated. The residue is crystallized from a mixture of 4-methyl-2-pentanone and 2,2'-oxybispropane. The product is filtered off and dried, yielding 1-(3-chloropropyl)-2-(phenylmethyl)-1H-benzimidazole; mp. 112° C.

EXAMPLE XX

A mixture of 30 parts of 3-[(2-amino-4-chlorophenyl)amino]-1-propanol, 44.8 parts of sodium α-hydroxybenzeneethanesulfonate and 120 parts of ethanol is stirred and refluxed for 30 minutes. The reaction mixture is evaporated and the residue is taken up in water. The oily product is extracted with trichloromethane. The extract is dried, filtered and evaporated, yielding 5-chloro-2-(phenylmethyl)-1H-benzimidazole-1-propanol as a residue.

EXAMPLE XXI

To a stirred mixture of 93 parts of 3-(2-aminophenyl)amino-1-propanol, 45.5 parts of potassium hydroxide and 600 parts of an ethanol solution 85% in water are added dropwise 60.8 parts of carbon disulfide. Upon completion, stirring is continued for 6 hours at reflux temperature. The reaction mixture is evaporated and the residue is taken up in 1500 parts of water. The whole is filtered over hyflo and the filtrate is acidified with acetic acid. The oily product solidifies on scratching. It is filtered off, washed with water and dried, yielding 2-mercapto-1H-benzimidazole-1-propanol; mp. 110° C.

A mixture of 20.8 parts of 2-mercapto-1H-benzimidazole-1-propanol, 15.62 parts of iodomethane and 120 parts of methanol is stirred overnight at room temperature. The reaction mixture is evaporated and the residue is dissolved in 500 parts of water. The solution is filtered over hyflo and the filtrate is alkalized with solid potassium hydroxide. The oily product is extracted with trichloromethane. The extract is dried, filtered and evaporated, yielding 2-(methylthio)-1H-benzimidazole-1-propanol as a residue.

To a stirred mixture of 19 parts of 2-(methylthio)-1H-benzimidazole-1-propanol, 15.2 parts of N,N-diethylethanamine and 195 parts of dichloromethane are added dropwise 11.5 parts of methanesulfonyl chloride. Upon completion, stirring is continued for one hour at reflux. After cooling, water is added and the layers are separated. The organic phase is dried, filtered and evaporated, yielding 3-[2-(methylthio)-1H-benzimidazol-1-yl]propyl methanesulfonate as an oily residue.

EXAMPLE XXII

A mixture of 40 parts of 3-[(2-amino-5-chlorophenyl)amino]-1-propanol, 87 parts of sodium α-hydroxycyclohexanemethanesulfonate and 200 parts of ethanol is stirred and refluxed for 10 minutes. The reaction mixture is diluted with water and the solvent is evaporated. The residue is extracted a few times with trichloromethane. The combined extracts are dried, filtered and evaporated. The oily residue is triturated in 2,2'-oxybispropane: a sticky tar precipitates. The 2,2'-oxybispropane is decanted and upon stirring at room temperature, the product is allowed to precipitate. It is filtered off and dried, yielding 6-chloro-2-cyclohexyl-1H-benzimidazole-1-propanol; mp. 120.1° C.

To a stirred mixture of 50 parts of 6-chloro-2-cyclohexyl-1H-benzimidazole-1-propanol in 375 parts of trichloromethane are added dropwise 60 parts of sulfinyl chloride (exothermic reaction). Upon completion, stirring is continued for 2 hours at reflux temperature. The reaction mixture is evaporated and the semisolid residue is dissolved in hot water. The solution is stirred with activated charcoal. The latter is filtered hot over hyflo and the filtrate is stirred in an ice-bath. The precipitated product is filtered off and dried, yielding 6-chloro-1-(3-chloropropyl)-2-cyclohexyl-1H-benzimidazole hydrochloride; mp. 227.5° C.

EXAMPLE XXIII

To a stirred and refluxing mixture of 7 parts of 2-ethyl-1H-benzimidazole-1-ethanol and 150 parts of trichloromethane are added dropwise 16 parts of sulfinyl chloride. Upon completion, the whole is heated to reflux and stirring is continued for 2 hours at reflux temperature. The reaction mixture is cooled and evaporated. Water is added to the residue and the whole is stirred with activated charcoal. The latter is filtered off and the filtrate is alkalized. The product is extracted with trichloromethane. The extract is dried, filtered and evaporated. The residue is crystallized from 2,2'-oxybispropane. The product is filtered off and dried, yielding 1-(2-chloroethyl)-2-ethyl-1H-benzimidazole.

EXAMPLE XXIV

A mixture of 30 parts of 1H-benzimidazole, 49 parts of 2-(4-chlorobutoxy)-tetrahydro-2H-pyran, 21 parts of potassium hydroxide and 200 parts of ethanol is stirred and refluxed overnight. The reaction mixture is cooled to room temperature, filtered and the filtrate is evaporated. The residue is stirred in water and acidified with a diluted hydrochloric acid solution. The whole is stirred and heated for 30 minutes in a water-bath. After cooling to room temperature, the product is extracted with methylbenzene. The aqueous phase is separated and alkalized with ammonium hydroxide. The product is extracted wit dichloromethane. The extract is dried, filtered and evaporated, yielding 1H-benzimidazole-1-butanol as an oily residue.

To a stirred mixture of 50 parts of 1H-benzimidazole-1-butanol and 375 parts of trichloromethane are added dropwise 35.2 parts of sulfinyl chloride. Upon completion, stirring is continued for 3 hours at reflux temperature. The reaction mixture is evaporated. The residue is taken up in trichloromethane. The whole is washed with ammonium hydroxide and the solvent is evaporated. The residue is purified by column-chromatography over silica gel using trichloromethane as eluent. The pure fractions are collected and the eluent is evaporated, yielding 1-(4-chlorobutyl)-1H-benzimidazole as an oily residue.

EXAMPLE XXV

A mixture of 113.2 parts of 1,2,4-trichloro-5-nitrobenzene, 75 parts of 3-amino-1-propanol, 0.2 parts of potassium iodide and 200 parts of butanol is stirred and refluxed overnight. The butanol is removed by evaporation in vacuo and water is added to the residue. The product is extracted with 4-methyl-2-pentanone. The extract is washed a few times with water, dried, filtered and evaporated. The oily residue is purified by column-chromatography over silica gel using a mixture of trichloromethane and 5% of methanol as eluent. The pure fractions are collected and the eluent is evaporated. The residue is triturated in 2,2'-oxybispropane. The product is filtered off and crystallized from a mixture of 2,2'-oxybispropane and 2-propanol, yielding 3-[(4,5-dichloro-2-nitrophenyl)amino]-1-propanol; mp. 97° C.

To a stirred mixture of 10 parts of 3-[(4,5-dichloro-2-nitrophenyl)amino]-1-propanol and 75 parts of trichloromethane are added dropwise 11.2 parts of sulfinyl chloride. Upon completion, stirring is continued for 4 hours at reflux temperature. The reaction mixture is evaporated and the residue is purified by column-chromatography over silica gel using a mixture of trichloromethane and methanol (98:2) as eluent. The pure fractions are collected and the eluent is evaporated. The residue is crystallized from 2,2'-oxybispropane. The product is filtered off and dried, yielding 4,5-dichloro-N-(3-chloropropyl)-2-nitrobenzenamine; mp. 78° C.

A mixture of 6.5 parts of 4,5-dichloro-N-(3-chloropropyl) 2-nitrobenzenamine, 5.6 parts of 1-(diphenylmethyl)piperazine, 5.3 parts of sodium carbonate, 0.1 parts of potassium iodide and 200 parts of 4-methyl-2-pentanone is stirred and refluxed overnight. The reaction mixture is cooled to room temperature and water is added. The organic phase is separated, dried, filtered and evaporated, yielding N-(4,5-dichloro-2-nitrophenyl)-4-(diphenylmethyl)-1-piperazinepropanamine as a residue.

A mixture of 8 parts of N-(4,5-dichloro-2-nitrophenyl)-4-(diphenylmethyl)-1-piperazinepropanamine and 200 parts of methanol is hydrogenated at normal pressure and at room temperature with 2 parts of Raney-nickel catalyst. After the calculated amount of hydrogen is taken up, the catalyst is filtered off and the filtrate is evaporated, yielding 4,5-dichloro-$N^1$-{3-[4-(diphenylmethyl)-1-piperazinyl]propyl}-1,2-benzenediamine as an oily residue.

EXAMPLE XXVI

A mixture of 100 parts of 1-chloro-2-nitro-4-(trifluoromethyl)benzene, 90 parts of 3-amino-1-propanol and 200 parts of butanol is stirred and heated till reflux. Stirring at reflux is continued overnight. The reaction mixture is cooled and evaporated. Water is added to the residue and the whole is acidified with a hydrochloric acid solution. The product is extracted with methylbenzene. The extract is dried, filtered and evaporated. The solid residue is crystallized from petroleumether. The product is filtered off and dried, yielding 3-{[2-nitro-4-(trifluoromethyl)phenyl]amino}-1-propanol.

To a stirred mixture of 26 parts of 3-{[2-nitro-4-(trifluoromethyl)phenyl]amino}-1-propanol and 150 parts of trichloromethane are added dropwise 40 parts of sulfinyl chloride. Upon completion, stirring is continued overnight at reflux temperature. The reaction mixture is evaporated. The residue is purified by column-chromatography over silica gel using a mixture of trichloromethane and methanol (95:5) as eluent. The pure fractions are collected and the eluent is evaporated, yielding N-(3-chloropropyl)-2-nitro-4-(trifluoromethyl)benzenamine as a residue.

A mixture of 10 parts of N-(3-chloropropyl)-2-nitro-4-(trifluoromethyl)benzenamine, 8.11 parts of 1-(diphenylmethyl)piperazine, 8.37 parts of sodium carbonate, 0.1 parts of potassium iodide and 200 parts of 4-methyl-2-pentanone is stirred and refluxed overnight. The reaction mixture is cooled and water is added. The organic phase is separated, washed with water, dried, filtered and evaporated. The oily residue is crystallized from 2-propanol. The product is filtered off and dried, yielding 4-(diphenylmethyl)-N-[2-nitro-4-(trifluoromethyl)phenyl]-1-piperazinepropanamine; mp. 113.7° C.

A mixture of 15 parts of 4-(diphenylmethyl)-N-[2-nitro-4-(trifluoromethyl)phenyl]-1-piperazinepropanamine in 240 parts of methanol is hydrogenated at normal pressure and at room temperature with 2 parts of Raney-nickel catalyst. After the calculated amount of hydrogen is taken up, the catalyst is filtered off and the filtrate is evaporated, yielding $N^1$-{3-[4-(diphenylmethyl)-1-piperazinyl]propyl}-4-(trifluoromethyl)-1,2-benzenediamine.

EXAMPLE XXVII

To a stirred mixture of 39.2 parts of 3-(2-nitrophenyl)amino-1-propanol and 225 parts of trichloromethane are added dropwise 35.7 parts of sulfinyl chloride (exothermic reaction: temperature rises to 45° C.) Upon completion, stirring is continued for 6 hours at reflux temperature. The reaction mixture is evaporated, yielding N-(3-chloropropyl)-2-nitrobenzenamine as a residue.

A mixture of 21.5 parts of N-(3-chloropropyl)-2-nitrobenzenamine, 22.68 parts of 1-(diphenylmethyl)-piperazine, 20 parts of N,N-diethylethanamine and 180 parts of N,N-dimethylacetamide is stirred and heated for 6 hours at 100° C. The reaction mixture is evaporated and the residue is taken up in water. The oily product is extracted with trichloromethane. The extract is dried, filtered and evaporated. The residue is crystallized from a mixture of 2-propanol, ethanol and 2,2'-oxybispropane. The product is filtered off and dried, yielding 4-(diphenylmethyl)-N-(2-nitrophenyl)-1-piperazinepropanamine hydrochloride; mp. 228° C.

A mixture of 15 parts of 4-(diphenylmethyl) N-(2-nitrophenyl)-1-piperazinepropanamine hydrochloride in 160 parts of methanol is hydrogenated at normal pressure and at room temperature with 5 parts of Raney-nickel catalyst. After the calculated amount of hydrogen is taken up, the catalyst is filtered off over hyflo and the filtrate is evaporated. The solid residue is crystallized from a mixture of 2-propanol and 2,2'-oxybispropane. The product is filtered off and dried, yielding N-(2-aminophenyl)-4-(diphenylmethyl)-1-piperazinepropanamine hydrochloride; mp. 223.1° C.

EXAMPLE XXVIII

A mixture of 50 parts of 1-chloro-2-nitro-4-(trifluoromethyl)benzene, 37 parts of 2-aminoethanol and 100 parts of 1-butanol is stirred and refluxed overnight. The reaction mixture is cooled and evaporated. The residue is taken up in a diluted hydrochloric acid solution. The product is extracted with methylbenzene. The layers are separated and the aqueous phase is extracted with methylbenzene. The combined methylbenzene-phases are washed successively with a diluted hydrochloric acid solution and twice with water, dried, filtered and evaporated. The solid residue is crystallized from petroleumether. The product is filtered off and dried, yielding 2-{[2-nitro-4-(trifluoromethyl)phenyl]amino}ethanol; mp. 74.9° C.

To a stirred mixture of 12.5 parts of 2-{[2-nitro-4-(trifluoromethyl)phenyl]amino}ethanol and 150 parts of trichloromethane are added dropwise 7.5 parts of sulfinyl chloride. Upon completion, stirring is continued for 2 hours at reflux temperature. The reaction mixture is evaporated and the residue is crystallized from 2,2'-oxybispropane. The product is filtered off and dried, yielding N-(2-chloroethyl)-2-nitro-4-(trifluoromethyl)-benzenamine.

A mixture of 9 parts of N-(2-chloroethyl)-2-nitro-4-(trifluoromethyl)benzenamine, 7.65 parts of 1-(diphenylmethyl)piperazine, 7.9 parts of sodium carbonate, 0.1 parts of potassium iodide and 200 parts of 4-methyl-2-pentanone is stirred and refluxed overnight. The reaction mixture is cooled, water is added and the layers are separated. The organic phase is dried, filtered and evaporated. The residue is crystallized from a mixture of 2,2'-oxybispropane and 2-propanol. The product is filtered off and dried, yielding 4-(diphenylmethyl)-N-[2-nitro-4-(trifluoromethyl)phenyl]-1-piperazineethanamine; mp. 152.1° C.

A mixture of 7.5 parts of 4-(diphenylmethyl)-N-[2-nitro-4-(trifluoromethyl)phenyl]-1-piperazineethanamine in 200 parts of methanol is hydrogenated at normal pressure and at room temperature with 5 parts of Ra/Ni. After the calculated amount of hydrogen is taken up, the catalyst is filtered off and the filtrate is evaporated, yielding $N^1$-{2-[4-(diphenylmethyl)-1-piperazinyl]ethyl}-4-(trifluoromethyl)-1,2-benzenediamine as an oily residue.

EXAMPLE XXIX

A mixture of 70.4 parts of 1-(phenylmethyl)piperazine, 39.4 parts of 1-(2-chloroethyl)-1,3-dihydro-2H-benzimidazol-2-one and 360 parts of methylbenzene is stirred and refluxed overnight. The reaction mixture is cooled, water is added and the layers are separated. The methylbenzene-phase is washed three times with water, dried, filtered and evaporated. The solid residue is purified by column-chromatography over silica gel using a mixture of trichloromethane and methanol (95:5) as eluent. The pure fractions are collected and the eluent is evaporated. The residue is boiled in 2,2'-oxybispropane. The whole is cooled on an ice-bath. The product is filtered off and crystallized from a mixture of 2,2'-oxybispropane and a small amount of 2-propanol, yielding 1,3-dihydro-1-{2-[4-(phenylmethyl)-1-piperazinyl]ethyl}-2H-benzimidazol-2-one; mp. 136.5° C.

A mixture of 79 parts of 1,3-dihydro-1-{2-[4-(phenylmethyl)-1-piperazinyl]ethyl}-2H-benzimidazol-2-one and 320 parts of methanol is hydrogenated at normal pressure and at room temperature with 10 parts of palladium-on-charcoal catalyst 10%. After the calculated amount of hydrogen is taken up, the catalyst is filtered off and the filtrate is evaporated. The oily residue is alkalized with ammonium hydroxide and a small amount of water is added. The product is extracted with trichloromethane. The extract is dried, filtered and evaporated. The oily residue solidifies on triturating in 4-methyl-2-pentanone. The product is filtered off and dried, yielding 1,3-dihydro-1-[2-(1-piperazinyl)ethyl]-2H-benzimidazol-2-one; mp. 122.6° C.

EXAMPLE XXX

A mixture of 60.5 parts of 1-(3-chloropropyl)-1,3-dihydro-3-(1-methylethenyl)-2H-benzimidazol-2-one, 31.68 parts of 1-(phenylmethyl)piperazine, 21.2 parts of sodium carbonate, 0.1 parts of potassium iodide and 400 parts of 4-methyl-2-pentanone is stirred and refluxed for 20 hours with water-separator. The reaction mixture is cooled, water is added and the layers are separated. The organic phase is dried, filtered and evaporated, yielding 1,3-dihydro-1-(1-methylethenyl)-3-{3-[4-(phenylmethyl)-1-piperazinyl]propyl}-2H-benzimidazol-2-one as a residue.

To a stirred solution of 70 parts of 1,3-dihydro-1-(1-methylethenyl)-3-{3-[4-(phenylmethyl)-1-piperazinyl]propyl}-2H-benzimidazol-2-one in 240 parts of ethanol are added 55 parts of a hydrochloric acid solution 6 N. The whole is stirred for 2 hours at 40°–50° C. The reaction mixture is evaporated and the residue is taken up in a diluted ammonium hydroxide solution. The oily product is extracted with trichloromethane. The extract is dried, filtered and evaporated, yielding 1,3-dihydro-1-{3-[4-(phenylmethyl)-1-piperazinyl]propyl}-2H-benzimidazol-2-one as a residue.

A mixture of 63 parts of 1,3-dihydro-1-{3-[4-(phenylmethyl)-1-piperazinyl]propyl}-2H-benzimidazol-2-one in 400 parts of methanol is hydrogenated at normal pressure and at room temperature with 10 parts of palladium-on-charcoal catalyst 10%. After the calculated amount of hydrogen is taken up, the catalyst is filtered off over hyflo and the filtrate is evaporated. The residue is crystallized from a mixture of 4-methyl-2-pentanone and 2-propanol. The product is filtered off and dried, yielding 1,3-dihydro-1-[3-(1-piperazinyl)propyl]-2H-benzimidazol-2-one; mp. 157.5° C.

EXAMPLE XXXI

To a stirred and refluxing mixture of 23.4 parts of (4-chlorophenyl) (2-fluorophenyl)methanone in 280 parts of 2-propanol are added portionwise 3.7 parts of sodium borohydride. Upon completion, stirring is continued for 2 hours at reflux temperature (±80° C.). The reaction mixture is cooled and decomposed by the addition of water. The 2-propanol is evaporated and the residual product is extracted with trichloromethane. The extract is dried, filtered and evaporated, yielding 4-chloro-α-(2-fluorophenyl)benzenemethanol as a residue.

To a stirred mixture of 23.6 parts of 4-chloro-α-(2-fluorophenyl)benzenemethanol in 108 parts of benzene are added dropwise 24 parts of sulfinyl chloride. Upon completion, the whole is heated to reflux and stirring is continued first for 5 hours at reflux temperature and further overnight at room temperature. The benzene is evaporated and the residue is distilled, yielding 1-chloro-4-[α-chloro-α-(2-fluorophenyl)methyl]benzene; bp. 122°–125° C. at 0.1 mm. pressure.

To a stirred and heated (95° C.) mixture of 202 parts of piperazine and 720 parts of methylbenzene is added a solution of 120 parts of 1-chloro-4-[α-chloro-α-(2-fluorophenyl)methyl]benzene in 180 parts of methylbenzene. The whole is stirred first for 1.50 hours at a temperature below 105° C. with water-separator and further for 24 hours at 100° C. The reaction mixture is allowed to cool to room temperature, washed with water, dried, filtered and evaporated. The residue is distilled (bp. 90° C. at 0.2 mm. pressure). The distillate is crystallized from petroleumether. The product is filtered off, yielding a first fraction of 1-[α-(4-chlorophenyl)-α-(2-fluorophenyl)methyl]piperazine. A second fraction is allowed to crystallize from the filtrate, yielding 1-[α-(4-chlorophenyl)-α-(2-fluorophenyl)methyl]piperazine.

EXAMPLE XXXII

A mixture of 21.5 parts of ethyl 4-hydroxy-1-piperidinecarboxylate, 35.2 parts of bis(4-fluorophenyl)bromomethane and 8.6 parts of potassium carbonate is stirred and heated in an oil-bath at 140° C. for 3 hours. The reaction mixture is allowed to cool to room temperature and water is added. The product is extracted with methylbenzene. The extract is washed successively with water, a diluted hydrochloric acid solution and a sodium bicarbonate solution, dried, filtered and evaporated. The forerun is distilled off (bp. till 143° C. at 0.5–1 mm. pressure), yielding ethyl 4-[bis(4-fluorophenyl)methoxy]-1-piperidinecarboxylate as an oily residue.

A mixture of 29 parts of ethyl 4-[bis(4-fluorophenyl)methoxy]-1-piperidinecarboxylate, 25 parts of potassium hydroxide, 1 part of water and 160 parts of 2-propanol is stirred and refluxed for 4 hours. The solvent is evaporated and water is added to the residue. The product is extracted with methylbenzene. The extract is washed a few times with water, dried, filtered and evaporated. The oily residue is converted into the hydrochloride salt in 4-methyl-2-pentanone and 2-propanol at room temperature. The salt is filtered off and dried, yielding 4-[bis(4-fluorophenyl)methoxy]piperidine hydrochloride; mp. 161.8° C.

EXAMPLE XXXIII

A mixture of 17.3 parts of 1-(ethoxycarbonyl)-4-hydroxypiperidine, 24.7 parts of bromodiphenylmethane and 7 parts of potassium carbonate is stirred and heated in an oil-bath for 3 hours at 140° C. The reaction mixture is cooled, water is added and the product is extracted with methylbenzene. The extract is washed a few times with water, dried, filtered and evaporated. The oily residue is distilled, yielding ethyl 4-(diphenylmethoxy)-1-piperidinecarboxylate; bp. 150° C. at 0.4 mm. pressure.

A mixture of 24 parts of ethyl 4-(diphenylmethoxy)-1-piperidinecarboxylate, 20 parts of potassium hydroxide and 120 parts of 2-propanol is stirred and refluxed for 4 hours. The 2-propanol is evaporated. Water is added to the residue and the product is extracted with methylbenzene. The extract is washed three times with water, dried, filtered and evaporated. The oily residue is converted into the hydrochloride salt in 2-propanone and 2-propanol. The salt is filtered off and dried, yielding 4-(diphenylmethoxy)piperidine hydrochloride; mp. 209.8° C.

EXAMPLE XXXIV

To a stirred mixture of 20 parts of aluminium chloride and 100 parts of fluorobenzene are added dropwise 20.5 parts of 2,4-dichlorobenzoyl chloride. Upon completion, the mixture is heated to reflux and stirred at reflux temperature for 5 minutes. The reaction mixture is poured onto crushed ice and the product is extracted with 1,1'-oxybisethane. The extract is dried and evaporated, yielding 30 parts of (2,4-dichlorophenyl)(4-fluorophenyl) methanone as an oily residue.

EXAMPLE XXXV

Following the procedure of Example XXXIV there is prepared (4-fluorophenyl)(4-pyridinyl)methanone; mp. 85.5° C., by the reaction of 4-pyridinecarbonyl chloride hydrochloride with fluorobenzene.

EXAMPLE XXXVI

To a stirred and cooled (10°-15° C.) mixture of 25 parts of (2,4-dichlorophenyl)(4-fluorophenyl)methanone and 80 parts of methanol are added portionwise 4.9 parts of sodium borohydride at about 10° C. Upon completion, stirring is continued overnight at room temperature. The reaction mixture is diluted with water and the solvent is evaporated. The residue is taken up in water and the product is extracted with trichloromethane. The extract is washed with water, dried, filtered and evaporated, yielding 22 parts of 2,4-dichloro-α-(4-fluorophenyl)benzenemethanol as a residue.

EXAMPLE XXXVII

Following the procedure of Example XXXVI and using an equivalent amount of an appropriate diarylmethanone as a starting material there are prepared:
α-(4-fluorophenyl)-4-pyridinemethanol; mp. 138.2° C.;
α-(4-fluorophenyl)-3-pyridinemethanol hydrochloride; mp. 158.3° C.; and
4-methoxy-α-[3-(trifluoromethyl)phenyl]benzenemethanol as a residue.

EXAMPLE XXXVIII

A mixture of 22 parts of 2,4-dichloro-α-(4-fluorophenyl)benzenemethanol and 240 parts of hydrochloric acid solution 12 N is stirred for 40 hours at room temperature. The reaction mixture is poured onto ice-water and the product is extracted with trichloromethane. The extract is washed with water, dried, filtered and evaporated. The residue is distilled, yielding 13.2 parts of 2,4-dichloro-1-[chloro-(4-fluorophenyl)methyl]benzene; bp. 146° C. at 0.15 mm. pressure.

EXAMPLE XXXIX

Following the procedure of Example XXXVIII and using an equivalent amount of an appropriate diarylmethanol as a starting material there are prepared:
1-[α-chloro-α-(4-methoxyphenyl)methyl]-3-(trifluoromethyl)benzene as a residue; and
1-[chloro-(4-methylphenyl)methyl]-4-fluorobenzene as a residue.

EXAMPLE XL

To a stirred mixture of 59 parts of α-(4-fluorophenyl)-3-pyridinemethanol hydrochloride in 150 parts of trichloromethane are added slowly 59.5 parts of sulfinyl chloride. Stirring is continued for 2 hours at reflux temperature. The reaction mixture is evaporated, yielding 64 parts (100%) of 3-[α-chloro-α-(4-fluorophenyl)methyl]pyridine hydrochloride as an oily residue.

EXAMPLE XLI

Following the procedure of Example XL and using an equivalent amount of an appropriate diarylmethanol as a starting material, there are prepared:
3-[α-chloro-α-(4-chlorophenyl)methyl]pyridine hydrochloride as a residue;
4-[α-chloro-α-(4-fluorophenyl)methyl]pyridine hydrochloride; mp. 198°-200° C.;
1-(chlorophenylmethyl)-2,3-dimethylbenzene; bp. 137° C. at 0.7 mm. pressure;
1-(chlorophenylmethyl)-2,4-dimethylbenzene; bp. 137° C. at 0.7 mm. pressure;
2-(chlorophenylmethyl)-1,4-dimethylbenzene; bp. 136° C. at 0.7 mm. pressure; and
1-(chlorophenylmethyl)-2-fluorobenzene; bp. 108°-109° C. at 0.4 mm. pressure.

EXAMPLE XLII

A mixture of 121 parts of piperazine, 54 parts of 3-[α-chloro-α-(4-chlorophenyl)methyl]pyridine hydrochloride and 315 parts of N,N-dimethylformamide is stirred for 20 hours at room temperature. The reaction mixture is evaporated and 250 parts of water are added to the residue. The product is extracted with methylbenzene. The organic phase is washed with water and extracted with an acetic acid solution 10%. The acid aqueous phase is alkalized with a sodium hydroxide solution 60% and the product is extracted again with methylbenzene. The extract is dried, filtered and evaporated. The oily residue is converted into the nitrate salt in ethanol. The salt is filtered off, washed with ethanol and with 2,2'-oxybispropane and crystallized from ethanol, yielding 48 parts of 1-[α-(4-chlorophenyl)-α-(3-pyridinyl)methyl]piperazine trinitrate; mp. 132.9° C.

EXAMPLE XLIII

Following the procedure of Example XLII and using equivalent amounts of the appropriate starting materials, there are prepared:
1-[α-(4-fluorophenyl)-α-(4-pyridinyl)methyl]piperazine; mp. 108.4° C.;
1-[(2-chlorophenyl)(3-chlorophenyl)methyl]piperazine;
1-[(2-fluorophenyl)phenylmethyl]piperazine ethanedioate (1:1); mp. 195.5° C.;
1-[(4-fluorophenyl)-(4-methoxyphenyl)methyl]piperazine ethanedioate (1:2); mp. 280.1° C.; and
1-[(4-nitrophenyl)phenylmethyl]piperazine dihydrochloride.

EXAMPLE XLIV

A mixture of 5.3 parts of 1-(3-chloropropyl)-1,3-dihydro-2H-benzimidazol-2-one, 5 parts of 1-(diphenylmethyl)piperazine, 6.4 parts of sodium carbonate and 200 parts of 4-methyl-2-pentanone is stirred and refluxed overnight with water-separator. After cooling, water is added and the layers are separated. The 4-methyl-2-pentanone-phase is dried, filtered and evaporated. The residue is purified by column-chromatography over silica gel using a mixture of trichloromethane and 5% of methanol as eluent. The pure fractions are collected and the eluent is evaporated. The oily residue is crystallized from a mixture of 2,2'-oxybispropane and a small amount of 2-propanol. The product is filtered off and dried, yielding 1-{3-[4-(diphenylmethyl)-1-piperazinyl]- propyl}-1,3-dihydro-2H-benzimidazol-2-one; mp. 153.6° C.

EXAMPLE XLV

Following the procedure of Example XLIV and using equivalent amounts of respectively an appropriate 1-(chloroalkyl)-1,3-dihydro-2H-benzimidazol-2-one and an appropriate 1-(diarylmethyl)piperazine as starting materials, the following compounds are obtained:

5-chloro-1-{3-[4-(diphenylmethyl)-1-piperazinyl]propyl}-1,3-dihydro-2H-benzimidazol-2-one; mp. 175° C.;

6-chloro-1-{3-[4-(diphenylmethyl)-1-piperazinyl]propyl}-1,3-dihydro-2H-benzimidazol-2-one; mp. 206.1° C.;

1-[2-{4-[bis(4-fluorophenyl)methyl]-1-piperazinyl}ethyl]-1,3-dihydro-2H-benzimidazol-2-one, hemihydrate; mp. 132° C.

1-[2-{4-[α-(4-fluoropheyl)-α-phenylmethyl]-1-piperazinyl}ethyl]-1,3-dihydro-2H-benzimidazol-2-one; mp. 172.4° C.; and 1-{2-[4-(diphenylmethyl)-1-piperazinyl]ethyl}-1,3-dihydro-5-methyl-2H-benzimidazol-2-one; mp. 214.6° C.

EXAMPLE XLVI

A mixture of 42.6 parts of 1-(3-chloropropyl)-1,3-dihydro-3-(1-methylethenyl)-2H-benzimidazol-2-one, 38 parts of 1-(diphenylmethyl)piperazine, 48 parts of sodium carbonate and 400 parts of 4-methyl-2-pentanone is stirred and refluxed overnight with water-separator. The reaction mixture is cooled, water is cooled and the layers are separated. The 4-methyl-2-pentanone-phase is washed with water, dried, filtered and evaporated. The oily residue is purified by column-chromatography over silica gel using a mixture of trichloromethane and 5% of methanol as eluent. The pure fractions are collected and the eluent is evaporated, yielding 1-{3-[4-(diphenylmethyl)-1-piperazinyl]propyl}-1,3-dihydro-3-(1-methylethenyl)-2H-benzimidazol-2-one as a residue.

EXAMPLE XLVII

By repeating the procedure of Example XLVI and using an equivalent amount of an appropriately substituted 1-(3-chloropropyl)-1,3-dihydro-3-(1-methylethenyl)-2H-benzimidazole as a starting material, there are prepared:

1-{3-[4-(diphenylmethyl)-1-piperazinyl]propyl}-1,3-dihydro-5-methyl-3-(1-methylethenyl)-2H-benzimidazol-2-one as an oily residue; and 3-{3-[4-(diphenylmethyl)-1-piperazinyl]propyl}-1,3-dihydro-5-methyl-1-(1-methylethenyl)-2H-benzimidazol-2-one as an oily residue.

EXAMPLE XLVIII

A mixture of 4.5 parts of 1-(2-chloroethyl)-2,3-dihydro-1H-benzimidazol-2-one, 5 parts of 1-(diphenylmethyl)piperazine, 6.4 parts of sodium carbonate and 200 parts of 4-methyl-2-pentanone is stirred and refluxed overnight with water-separator. The reaction mixture is cooled and water is added. The precipitated product is filtered off and crystallized from a mixture of N,N-dimethylformamide and water, yielding 1-{2-[4-(diphenylmethyl)-1-piperazinyl]ethyl}-1,3-dihydro-2H-benzimidazol-2-one; mp. 218° C.

EXAMPLE IL

A mixture of 2.7 parts of 1,3-dihydro-1-(3-hydroxypropyl)-2H-benzimidazol-2-one methanesulfonate, 2.88 parts of 1-[bis(p-fluorophenyl)methyl]piperazine, 2.66 parts of sodium carbonate and 100 parts of 4-methyl-2-pentanone is stirred and refluxed overnight. After cooling, water is added and the layers are separated. The organic phase is dried, filtered and evaporated. The residue is purified by column-chromatography over silica gel using a mixture of trichloromethane and 5% of methanol as eluent. The pure fractions are collected and the eluent is evaporated. The residue is crystallized from 2-propanol, yielding 1-[3-{4-[bis(4-fluorophenyl)methyl]-1-piperazinyl}propyl]-1,3-dihydro-2H-benzimidazol-2-one; mp. 197.3° C.

EXAMPLE L

A mixture of 4.6 parts of 1-(3-chlorophenyl)-1,3-dihydro-2H-benzimidazol-2-one, 5.4 parts of 1-(p-fluoro-α-phenylbenzyl)piperazine, 15 parts of sodium carbonate, 0.2 parts of potassium iodide and 80 parts of 4-methyl-2-pentanone is stirred and refluxed overnight. After cooling, water is added and the layers are separated. The organic phase is dried, filtered and evaporated. The residue is boiled in 2,2'-oxybispropane with activated charcoal. The latter is filtered off and the product is allowed to crystallize from the filtrate while stirring. It is filtered off and crystallized from 4-methyl-2-pentanone, yielding 1-[3-{4-[α-(4-fluorophenyl)-α-phenylmethyl]-1-piparazinyl}propyl]-1,3-dihydro-2H-benzimidazol-2-one; mp. 153.6° C.

EXAMPLE LI

Following the procedure of Example L and using equivalent amounts of the appropriate starting materials, the following compounds are prepared:

1-[3-{4-[α-(4-chlorophenyl)-α-phenylmethyl]-1-piperazinyl}propyl]-1,3-dihydro-2H-benzimidazol-2-one; mp. 180.2° C.;

1-[3-{4-[α-(4-chlorophenyl)-α-(2-fluorophenyl)methyl]-1-piperazinyl}propyl]-1,3-dihydro-2H-benzimidazol-2-one; mp. 136° C.;

1-[3-{4[bis(4-fluorophenyl)methyl]-1-piperazinyl}propyl]-5-chloro-1,3-dihydro-2H-benzimidazol-2-one; mp. 205.8° C.;

1-[3-{4-[bis(4-fluorophenyl)methyl]-1-piperazinyl}propyl]-6-chloro-1,3-dihydro-2H-benzimidazol-2-one hydrate; mp. 132.9° C.;

1-{4-[4-(diphenylmethyl)-1-piperazinyl]butyl}-1,3-dihydro-2H-benzimidazol-2-one; mp. 196.6° C.;

6-chloro-1-{2-[4-(diphenylmethyl)-1-piperazinyl]ethyl}-1,3-dihydro-2H-benzimidazol-2-one; mp. 204.1° C.;

5-chloro-1-{2-[4-(diphenylmethyl)-1-piperazinyl]ethyl}-1,3-dihydro-2H-benzimidazol-2-one; mp. 203.6° C.; and 1-{4-[4-(diphenylmethyl)-1-piperazinyl]butyl}-1,3-dihydro-2H-benzimidazol-2-one hemihydrate; mp. 197.8° C.

EXAMPLE LII

A mixture of 6 parts of 1-(3-chlorophenyl)-1,3-dihydro-3-(phenylmethyl)-2H-benzimidazol-2-one, 4.5 parts of 1-(diphenylmethyl)piperazine, 5.3 parts of sodium carbonate, 0.1 parts of potassium iodide and 200 parts of 4-methyl-2-pentanone is stirred and refluxed for 20 hours with water-separator. The reaction mixture is cooled, water is added and the layers are separated. The organic phase is dried, filtered and evaporated. The residue is converted into the hydrochloride salt in 2,2'-oxybispropane and 2-propanol. The salt is filtered off and crystallized from 2-propanone, yielding 1-{3-[4-(diphenylmethyl)-1-piperazinyl]propyl}-1,3-dihydro-3-(phenylmethyl)-2H-benzimidazol-2-one dihydrochloride; mp. 199.6° C.

EXAMPLE LIII

A mixture of 4.94 parts of 1-(4-chlorobutyl)-1,3-dihydro-2H-benzimidazol-2-one, 5.76 parts of 1-[bis(4-fluorophenyl)methyl]piperazine, 5.3 parts of sodium carbonate, 0.2 parts of potassium iodide and 200 parts of 4-methyl-2-pentanone is stirred and refluxed for 20 hours with water-separator. The reaction mixture is cooled, water is added and the layers are separated. The organic phase is dried, filtered and evaporated. The residue is crystallized from ethanol. The product is filtered off and dried, yielding 1-[4-{4-[bis(4-fluorophenyl)methyl]-1-piperazinyl}butyl]-1,3-dihydro-2H-benzimidazol-2-one dihydrochloride. hydrate; mp. 184.4° C.

EXAMPLE LIV

A mixture of 12 parts of 1-(3-chloro-2-methylpropyl)-1,3-dihydro-3-(1-methylethenyl)-2H-benzimidazol-2-one, 5.76 parts of 1-[bis(4-fluorophenyl)methyl]piperazine, 5.3 parts of sodium carbonate, 0.2 parts of potassium iodide and 200 parts of 4-methyl-2-pentanone is stirred and refluxed for 20 hours with water-separator. The reaction mixture is cooled, water is added and the layers are separated. The organic phase is dried, filtered and evaporated, yielding 1-[3-{4-[bis(4-fluorophenyl)methyl]-1-piperazinyl}-2-methylpropyl]-1,3-dihydro-3-(1-methylethenyl)-2H-benzimidazol-2-one as an oily residue.

EXAMPLE LV

Following the procedure of Example LIV and using equivalent amounts of the appropriate starting materials, there are prepared:
1-[3-{4-[(4-chlorophenyl)(3-pyridinyl)methyl]-1-piperazinyl}propyl]-1,3-dihydro-3-(1-methylethenyl)-2H-benzimidazol-2-one as a residue;
1-[3-{4-[(4-fluorophenyl)(4-pyridinyl)methyl]-1-piperazinyl}propyl]-1,3-dihydro-3-(1-methylethenyl)-2H-benzimidazol-2-one as a residue;
1-[3-{4-[(4-chlorophenyl)(4-methoxyphenyl)methyl]-1-piperazinyl}propyl]-1,3-dihydro-3-(1-methylethenyl)-2H-benzimidazol-2-one as a residue;
1,3-dihydro-1-[3-{4-[(4-nitrophenyl)phenylmethyl]-1-piperazinyl}propyl]-2H-benzimidazol-2-one; mp. 103.6° C.;
1-[3-{4-[(2-fluorophenyl)phenylmethyl]-1-piperazinyl}propyl]-1,3-dihydro-3-(1-methylethenyl)-2H-benzimidazol-2-one as a residue;
1-[3-{4-[(4-fluorophenyl)(4-methoxyphenyl)methyl]-1-piperazinyl}propyl]-1,3-dihydro-2H-benzimidazol-2-one; mp. 157.4° C.; and
1-[3-{4-[(4-bromophenyl)phenylmethyl]-1-piperazinyl}propyl]-1,3-dihydro-2H-benzimidazol-2-one; mp. 189.7° C.

EXAMPLE LVI

A mixture of 4.94 parts of 1-(4-chlorobutyl)-1,3-dihydro-2H-benzimidazol-2-one, 5.76 parts of 1-[bis(4-fluorophenyl)methyl]piperazine, 5.3 parts of sodium carbonate, 0.1 parts of potassium iodide and 200 parts of 4-methyl-2-pentanone is stirred and refluxed for 20 hours with water-separator. After cooling, water is added and the layers are separated. The organic phase is dried, filtered and evaporated. The residue is crystallized from ethanol. The product is filtered off and dried, yielding 1-[4-{4-[bis(4-fluorophenyl)methyl]-1-piperazinyl}butyl]-1,3-dihydro-2H-benzimidazol-2-one dihydrochloride. hydrate. hemiethanolate; mp. 172.9° C.

EXAMPLE LVII

A mixture of 5.5 parts of 1,3-dihydro-1-(3-iodopropyl)-3-methyl-2H-benzimidazol-2-one, 3.8 parts of 1-(diphenylmethyl)piperazine, 4 parts of sodium carbonate and 200 parts of 4-methyl-2-pentanone is stirred and refluxed for 5 hours. The reaction mixture is cooled to room temperature and water is added. The organic phase is separated, dried, filtered and evaporated. The residue is purified by column-chromatography over silica gel using a mixture of trichloromethane and methanol (95:5) as eluent. The pure fractions are collected and the eluent is evaporated. The residue is converted into the hydrochloride salt in 2-propanol and 1,1'-oxybisethane. The salt is filtered off and crystallized from ethanol, yielding 1-{3-[4-(diphenylmethyl)-1-piperazinyl]propyl}-1,3-dihydro-3-methyl-2H-benzimidazol-2-one dihydrochloride. hydrate; mp. 201.8° C.

EXAMPLE LVIII

A mixture of 4.2 parts of 1-(3-chloropropyl)-1,3-dihydro-2H-benzimidazol-2-one, 5.7 parts of 1-[α-(3-chlorophenyl)-α-phenylmethyl]piperazine, 4.75 parts of sodium carbonate, 0.1 parts of potassium iodide and 200 parts of 4-methyl-2-pentanone is stirred and refluxed overnight. After cooling, water is added and the layers are separated. The organic phase is dried, filtered and evaporated. The residue is purified by column-chromatography over silica gel using a mixture of trichloromethane and methanol (95:5 by volume) as eluent. The pure fractions are collected and the eluent is evaporated. The residue is crystallized from a mixture of 4-methyl-2-pentanone and 2,2'-oxybispropane. The product is filtered off and recrystallized from 4-methyl-2-pentanone, yielding 1-[3-{4-[α-(3-chlorophenyl)-α-phenylmethyl]-1-piperazinyl}propyl]-1,3-dihydro-2H-benzimidazol-2-one; mp. 112.7° C.

EXAMPLE LIX

Following the procedure of Example LVIII and using equivalent amounts of the appropriate starting materials, the following compounds are prepared in free base form or in the form of a hydrochloride salt after treatment of the base with hydrochloric acid in ethanol.
4-chloro-3-{3-[4-(diphenylmethyl)-1-piperazinyl]propyl}-1,3-dihydro-2H-benzimidazol-2-one; mp. 196.9° C.; and
5-chloro-1-{3-[4-(diphenylmethyl)-1-piperazinyl]propyl}-1,3-dihydro-3-phenyl-2H-benzimidazol-2-one dihydrochloride. hemihydrate; mp. 184.2° C.

EXAMPLE LX

A mixture of 5.4 parts of 3-(3-bromopropyl)-2(3H)-benzothiazolone, 4.5 parts of 1-(diphenylmethyl)piperazine, 5.3 parts of sodium carbonate, 0.1 parts of potassium iodide and 200 parts of 4-methyl-2-pentanone is stirred and refluxed for 4 hours with water-separator.

After cooling, water is added and the layers are separated. The organic phase is dried, filtered and evaporated. The residue is converted into the hydrochloride salt in 2,2'-oxybispropane and 2-propanol. The salt is filtered off and crystallized from ethanol, yielding 3-{3-[4-(diphenylmethyl)-1-piperazinyl]propyl}-2(3H)-benzothiazolone dihydrochloride.hemihydrate; mp. 186.1° C.

EXAMPLE LXI

A mixture of 4.9 parts of 3-(3-chloropropyl)-2(3H)-benzoxazolone, 5 parts of 1-(diphenylmethyl)piperazine, 6.4 parts of sodium carbonate and 200 parts of 4-methyl-2-pentanone is stirred and refluxed overnight with water-separator. The reaction mixture is cooled, water is added and the layers are separated. The 4-methyl-2-pentanone phase is dried, filtered and evaporated. The oily residue is dissolved in 2,2'-oxybispropane and the solution is stirred with activated charcoal. The latter is filtered off over hyflo and the clear filtrate is acidified with 2-propanol, previously saturated with gaseous hydrogen chloride. The formed hydrochloride salt is filtered off and triturated in 2-propanol. It is filtered off again and dried, yielding 3-{3-[4-(diphenylmethyl)-1-piperazinyl]propyl}-2(3H)benzoxazolone dihydrochloride; mp. 212.4° C.

EXAMPLE LXII

A mixture of 4.9 parts of 1-(3-chloropropyl)-1H-benzimidazole, 5.76 parts of 1-[bis(4-fluorophenyl)methyl]piperazine, 5.3 parts of sodium carbonate, 0.1 parts of potassium iodide and 200 parts of 4-methyl-2-pentanone is stirred and refluxed for 20 hours with water-separator. The reaction mixture is cooled, water is added and the layers are separated. The organic phase is dried, filtered and evaporated. The residue is crystallized from a mixture of 4-methyl-2-pentanone and 2,2'-oxybispropane. The product is filtered off and dried, yielding 1-[3-{4-[bis(4-fluorophenyl)methyl]-1-piperazinyl}propyl]-1H-benzimidazole hydrate; mp. 108.4° C.

EXAMPLE LXIII

Following the procedure of Example LXII and using equivalent amounts of the appropriate starting materials, the following compounds are obtained in free base form or in the form of a hydrochloride salt after treatment of the base with hydrochloric acid.
1-{2-[4-(diphenylmethyl)-1-piperazinyl]ethyl}-1H-benzimidazole; mp. 192.3° C.;
1-[3-{4-[(3-chlorophenyl)phenylmethyl]-1-piperazinyl}propyl]-1H-benzimidazole trihydrochloride.hydrate.hemi-2-propanolate; mp. 191.1° C.;
1-{3-[4-(diphenylmethyl)-1-piperazinyl]propyl}-2-phenyl-1H-benzimidazole; mp. 130.5° C.;
6-chloro-1-{3-[4-(diphenylmethyl)-1-piperazinyl]propyl}-2-phenyl-1H-benzimidazole; mp. 143.9° C.;
1-{2-[4-(diphenylmethyl)-1-piperazinyl]ethyl}-2-phenyl-1H-benzimidazole trihydrochloride.hydrate; mp. 198.3° C.;
5-chloro-1-{3-[4-(diphenylmethyl)-1-piperazinyl]propyl}-2-phenyl-1H-benzimidazole; mp. 127.8° C.;
1-{3-[4-(diphenylmethyl)-1-piperazinyl]propyl}-2-(phenylmethyl)-1H-benzimidazole trihydrochloride.trihydrate; mp. 179.9° C.; and
5-chloro-1-{3-[4-(diphenylmethyl)-1-piperazinyl]propyl}-2-(phenylmethyl)-1H-benzimidazole trihydrochloride.hydrate; mp. 198.2° C.

EXAMPLE LXIV

A mixture of 4.5 parts of 1-(3-chloropropyl)-1H-benzimidazole, 5.1 parts of 1-(diphenylmethyl)piperazine, 3.7 parts of sodium carbonate, 0.1 parts of potassium iodide and 80 parts of 4-methyl-2-pentanone is stirred and refluxed overnight. The reaction mixture is cooled, water is added and the layers are separated. The organic phase is dried, filtered and evaporated. The residue is purified by column-chromatography over silica gel using a mixture of trichloromethane and methanol (95:5 by volume) as eluent. The pure fractions are collected and the eluent is evaporated. The residue is crystallized from a mixture of 4-methyl-2-pentanone and 2,2'-oxybispropane, yielding 1-{3-[4-(diphenylmethyl)-1-piperazinyl]propyl}-1H-benzimidazole; mp. 132.3° C.

EXAMPLE LXV

Following the procedure of Example LXIV and using equivalent amounts of the appropriate starting materials, the following compounds are prepared in free base form or in the form of a hydrochloride salt after treatment of the base with hydrochloric acid.
1-[3-{4-[(4-fluorophenyl)phenylmethyl]-1-piperazinyl}propyl]-1H-benzimidazole; mp. 102.5° C.;
1-[3-{4-[(4-chlorophenyl)phenylmethyl]-1-piperazinyl}propyl]-1H-benzimidazole; mp. 90.8° C.;
1-{4-[4-(diphenylmethyl)-1-piperazinyl]butyl}-1H-benzimidazole; mp. 106° C.;
1-[4-{4-[(4-fluorophenyl)phenylmethyl]-1-piperazinyl}butyl]-1H-benzimidazole; mp. 114.9° C.;
1-[4-{4-[bis(4-fluorophenyl)methyl]-1-piperazinyl}butyl]-1H-benzimidazole; mp. 86.3° C.;
1-{3-[4-(diphenylmethyl)-1-piperazinyl]-2-methylpropyl}-1H-benzimidazole trihydrochloride.hemihydrate; mp. 237.3° C.;
1-[3-{4-[bis(4-fluorophenyl)methyl]-1-piperazinyl}-2-methylpropyl]-1H-benzimidazole trihydrochloride.hemihydrate; mp. 223.4° C.;
1-{3-[4-(diphenylmethyl)-1-piperazinyl]propyl}-2-methyl-1H-benzimidazole; mp. 121.2° C.;
5-chloro-1-{3-[4-(diphenylmethyl)-1-piperazinyl]propyl}-2-methyl-1H-benzimidazole trihydrochloride.hydrate; mp. 226.4° C.;
1-{4-[4-(diphenylmethyl)-1-piperazinyl]butyl}-2-methyl-1H-benzimidazole; mp. 118.7° C.;
1-{2-[4-(diphenylmethyl)-1-piperazinyl]ethyl}-2-ethyl-1H-benzimidazole trihydrochloride.hydrate; mp. 208.5° C.;
1-{3-[4-(diphenylmethyl)-1-piperazinyl]propyl}-2-ethyl-1H-benzimidazole trihydrochloride.hydrate; mp. 224.5° C.;
5-chloro-1-{3-[4-(diphenylmethyl)-1-piperazinyl]propyl}-2-ethyl-1H-benzimidazole trihydrochloride.hydrate; mp. 233.1° C.;
2-cyclohexyl-1-{3-[4-(diphenylmethyl)-1-piperazinyl]propyl}-1H-benzimidazole; mp. 106.5° C.;
5-chloro-2-cyclohexyl-1-{3-[4-diphenylmethyl)-1-piperazinyl]propyl}-1H-benzimidazole; mp. 114.9° C.; and
6-chloro-2-cyclohexyl-1-{3-[4-(diphenylmethyl)-1-piperazinyl]propyl}-1H-benzimidazole; mp. 173.6° C.

EXAMPLE LXVI

A mixture of 4.9 parts of 1-(3-chloropropyl)-1H-benzimidazole, 7 parts of 1-[(2-chlorophenyl)phenylmethyl]piperazine acetate, 10.6 parts of sodium carbonate, 0.1 parts of potassium iodide and 200 parts of 4-methyl- 2-pentanone is stirred and refluxed for 20 hours with water-separator. The reaction mixture is cooled, water is added and the layers are separated. The organic phase is dried, filtered and evaporated. The residue is converted into the hydrochloride salt in 2-propanol and 2,2'-oxybispropane. The salt is filtered off and crystallized from 2-propanol, yielding 1-[3-{4-[(2-chlorophenyl)phenylmethyl]-1-piperazinyl}propyl]-1H-benzimidazole trihydrochloride dihydrate; mp. 182.9° C.

EXAMPLE LXVII

A mixture of 6 parts of 3-[2-(methylthio)-1H-benzimidazol-1-yl]propyl methanesulfonate, 3.78 parts of 1-(diphenylmethyl)piperazine, 5.3 parts of sodium carbonate and 200 parts of 4-methyl-2-pentanone is stirred and refluxed for 5 hours with water-separator. After cooling, water is added and the layers are separated. The organic phase is dried, filtered and evaporated. The residue is converted into the hydrochloride salt in 2,2'-oxybispropane and 2-propanol. The salt is filtered off and crystallized from ethanol, yielding, after drying, 1-{3-[4-(diphenylmethyl)-1-piperazinyl]propyl}-2-(methylthio)-1H-benzimidazole trihydrochloride.hydrate; mp. 203.4° C.

EXAMPLE LXVIII

A mixture of 6.95 parts of 1-(5-chloropentyl)-1,3-dihydro-3-(1-methylethenyl)-2H-benzimidazol-2-one, 5.15 parts of 1-(diphenylmethyl)piperazine, 5.30 parts of sodium carbonate, 0.1 parts of potassium iodide and 160 parts of 4-methyl-2-pentanone is stirred and refluxed overnight with water-separator. The reaction mixture is cooled to room temperature, water is added and the layers are separated. The organic phase is dried, filtered and evaporated. The residue is stirred and refluxed for 30 minutes with 12 parts of a hydrochloric acid solution in 40 parts of ethanol. The whole is evaporated and the residue is crystallized from ethanol, yielding 1-{5-[4-(diphenylmethyl)-1-piperazinyl]pentyl}-1,3-dihydro-2H-benzimidazol-2-one dihydrochloride.hydrate; mp. 215.3° C.

EXAMPLE LXIX

A mixture of 6.95 parts of 1-(5-chloropentyl)-1,3-dihydro-3-(1-methylethenyl)-2H-benzimidazol-2-one, 5.7 parts of 1-[bis(4-fluorophenyl)methyl]piperazine, 5.3 parts of sodium carbonate, 0.1 parts of potassium iodide and 160 parts of 4-methyl-2-pentanone is stirred and refluxed overnight. The reaction mixture is cooled to room temperature, water is added and the layers are separated. The organic phase is dried, filtered and evaporated. The residue is stirred and refluxed for 30 minutes with a solution of 12 parts of a concentrated hydrochloric acid solution in 40 parts of ethanol. The solvent is evaporated and the free base is liberated in the conventional manner with a diluted ammonium hydroxide solution. The product is extracted with trichloromethane. The extract is dried, filtered and evaporated. The residue is purified by column-chromatography over silica gel using a mixture of trichloromethane and methanol (90:10 by volume) as eluent. The pure fractions are collected and the eluent is evaporated. The residue is converted into the hydrochloride salt in ethanol and 2-propanol. The salt is filtered off and dried, yielding 1-[5-{4-[bis(4-fluorophenyl)methyl]-1-piperazinyl}pentyl]-1,3-dihydro-2H-benzimidazol-2-one dihydrochloride.hydrate; mp. 203.7° C.

EXAMPLE LXX

Following the procedure of Example LXIX and using equivalent amounts of the appropriate starting materials, there are prepared:

1-[4-{4-[(4-fluorophenyl)phenylmethyl]-1-piperazinyl}butyl]-1,3-dihydro-2H-benzimidazol-2-one; mp. 172.3° C.;

1-[3-{4-[(2-chlorophenyl)phenylmethyl]-1-piperazinyl}propyl]-1,3-dihydro-2H-benzimidazol-2-one; mp. 149° C.;

1-[3-{4-[(2-chlorophenyl)(3-chlorophenyl)methyl]-1-piperazinyl}propyl]-1,3-dihydro-2H-benzimidazol-2-one hydrate; mp. 139.1° C.; and 1-[3-{4-[(2,4-dichlorophenyl)phenylmethyl]-1-piperazinyl}-propyl]-1,3-dihydro-2H-benzimidazol-2-one; mp. 160.1° C.

EXAMPLE LXXI

To a stirred solution of 76 parts of 1-{3-[4-(diphenylmethyl)-1-piperazinyl]propyl}-1,3-dihydro-3-(1-methylethenyl)-2H-benzimidazol-2-one in 280 parts of ethanol are added 120 parts of a hydrochloric acid solution and 250 parts of water. The whole is stirred for 30 minutes at room temperature. Upon cooling in an ice-bath, the product is precipitated. It is filtered off, washed with 2-propanone and with 2,2'-oxybispropane, and dried, yielding 1-{3-[4-(diphenylmethyl)-1-piperazinyl]propyl}-1,3-dihydro-2H-benzimidazol-2-one dihydrochloride.hydrate; mp. 237.5° C.

EXAMPLE LXXII

Following the procedure of Example LXXI and using equivalent amounts of the appropriate starting materials, there are prepared:

1-[3-{4-[(4-chlorophenyl)(3-pyridinyl)methyl]-1-piperazinyl}-propyl]-1,3-dihydro-2H-benzimidazol-2-one; mp. 160.2° C.;

1-[3-{4-[(4-fluorophenyl)(4-pyridinyl)methyl]-1-piperazinyl}propyl]-1,3-dihydro-2H-benzimidazol-2-one; mp. 183.2° C.;

1-[3-{4-[(4-chlorophenyl)(4-methoxyphenyl)methyl]-1-piperazinyl}propyl]-1,3-dihydro-2H-benzimidazol-2-one; mp. 199.3° C.; and 1-[3-{4-[(2-fluorophenyl)phenylmethyl]-1-piperazinyl}-propyl]-1,3-dihydro-2H-benzimidazol-2-one; mp. 157.7° C.

EXAMPLE LXXIII

A mixture of 7.3 parts of 1-(6-chlorohexyl)-1,3-dihydro-3-(1-methylethenyl)-2H-benzimidazol-2-one, 5.15 parts of 1-(diphenylmethyl)piperazine, 5.3 parts of sodium carbonate, 0.1 parts of potassium iodide and 160 parts of 4-methyl-2-pentanone is stirred and refluxed overnight with water-separator. The reaction mixture is cooled, water is added and the layers are separated. The organic phase is dried, filtered and evaporated. The residue is stirred and refluxed for one hour with 12 parts of a concentrated hydrochloric acid solution and 40 parts of ethanol. The solvent is evaporated and the residue is taken up in water. The free base is liberated in the conventional manner with ammonium hydroxide. The product is extracted with trichloromethane. The extract is dried, filtered and evaporated. The residue is crystallized from methanol. The product is filtered off and recrystallized from N,N-dimethylformamide, yielding 1-{6-[4-(diphenylmethyl)-1-piperazinyl]hexyl}-1,3-dihydro-2H-benzimidazol-2-one; mp. 189.7° C.

EXAMPLE LXXIV

A mixture of 3.65 parts of 1-(6-chlorohexyl)-1,3-dihydro-3-(1-methylethenyl)-2H-benzimidazol-2-one, 2.9 parts of 1-[bis(4-fluorophenyl)methyl]piperazine, 2.65 parts of sodium carbonate, 0.1 parts of potassium iodide and 80 parts of 4-methyl-2-pentanone is stirred and refluxed overnight. The reaction mixture is cooled, water is added and the layers are separated. The organic phase is dried, filtered and evaporated. The residue is stirred for 30 minutes with a solution of 12 parts of a concentrated hydrochloric acid solution in 40 parts of ethanol. The solvent is evaporated and the residue is dissolved in water. The free base is liberated in the conventional manner with ammonium hydroxide and extracted with trichloromethane. The extract is dried, filtered and evaporated. The residue is converted into the hydrochloride salt in ethanol and 2-propanol. The salt is filtered off and dried, yielding 1-[6-{4-[bis(4-fluorophenyl)methyl]-1-piperazinyl}hexyl]-1,3-dihydro-2H-benzimidazol-2-one dihydrochloride; mp. 204.5° C.

EXAMPLE LXXV

A mixture of 9.6 parts of 1-{3-[4-(diphenylmethyl)-1-piperazinyl]propyl}-1,3-dihydro-5-methyl-3-(1-methylethenyl)-2H-benzimidazol-2-one, 24 parts of a hydrochloric acid solution, 50 parts of water and 96 parts of ethanol is stirred first for a while at about 50° C. and further for 30 minutes at room temperature. The reaction mixture is evaporated and the oily residue is triturated in 2-propanone. The hydrochloride salt is filtered off and the free base is liberated in the conventional manner with ammonium hydroxide in water. The product is extracted with methylbenzene. The extract is dried, filtered and evaporated. The semi-solid residue is crystallized from a mixture of 2-propanol and 2,2'-oxybispropane. The product is filtered off and dried, yielding 1-{3-[4-(diphenylmethyl)-1-piperazinyl]propyl}-1,3-dihydro-5-methyl-2H-benzimidazol-2-one; mp. 178.3° C.

EXAMPLE LXXVI

To a stirred solution of 9.6 parts of 3-{3-[4-(diphenylmethyl)-1-piperazinyl]propyl}-1,3-dihydro-5-methyl-1-(1-methylethenyl)-2H-benzimidazol-2-one in 80 parts of ethanol are added 24 parts of a concentrated hydrochloric acid solution and 50 parts of water (exothermic reaction: temperature rises to 50° C.). Stirring is continued for 30 minutes at room temperature. The reaction mixture is evaporated and the residue is triturated in 2-propanone. The hydrochloride salt is filtered off and the free base is liberated in the conventional manner with ammonium hydroxide. Methylbenzene is added and the precipitated free base is filtered off. It is crystallized from a mixture of 2-propanol and a small amount of N,N-dimethylformamide, yielding 1-{3-[4-(diphenylmethyl)-1-piperazinyl]propyl}-1,3-dihydro-6-methyl-2H-benzimidazol-2-one; mp. 195.7° C.

EXAMPLE LXXVII

A stirred solution of 8 parts of 1-[3-{4-[bis(4-fluorophenyl)methyl]-1-piperazinyl}-2-methylpropyl]-1,3-dihydro-3-(1-methylethenyl)-2H-benzimidazol-2-one in 120 parts of ethanol is acidified with 2-propanol, previously saturated with gaseous hydrogen chloride. The whole is stirred and refluxed for 5 minutes. The reaction mixture is evaporated. The residue is taken up in water and the whole is alkalized with a concentrated ammonium hydroxide solution. The oily product is extracted with trichloromethane. The extract is dried, filtered and evaporated. The residue is crystallized from 4-methyl-2-pentanone. The product is filtered off and dried, yielding 1-[3-{4-[bis(4-fluorophenyl)methyl]-1-piperazinyl}-2-methylpropyl]-1,3-dihydro-2H-benzimidazol-2-one; mp. 176° C.

EXAMPLE LXXVIII

A mixture of 3.6 parts of $N^1$-{2-[4-(diphenylmethyl)-1-piperazinyl]ethyl}-4-(trifluoromethyl-1,2-benzendiamine and 1.8 parts of urea is stirred for 3 hours in an oil-bath at 190° C. The reaction mixture is cooled, water and trichloromethane are added and the layers are separated. The organic phase is dried, filtered and evaporated. The residue is purified by column-chromatography over silica gel using a mixture of trichloromethane and methanol (95:5 by volume) as eluent. The pure fractions are collected and the eluent is evaporated, yielding 1-{2-[4-(diphenylmethyl)-1-piperazinyl]ethyl}-1,3-dihydro-5-(trifluoromethyl)-2H-benzimidazol-2-one; mp. 163.7° C.

EXAMPLE LXXIX

A mixture of 5.4 parts of urea and 13.7 parts of $N^1$-{3-[4-(diphenylmethyl)-1-piperazinyl]propyl}-4-(trifluoromethyl)-1,2-benzenediamine is stirred and heated for 4 hours at 190° C. The reaction mixture is cooled to room temperature and diluted with water. After the addition of trichloromethane, the layers are separated. The aqueous phase is extracted with trichloromethane. The combined organic phases are washed with water, dried, filtered and evaporated. The oily residue is purified by column-chromatography over silica gel using trichloromethane and methanol (90:10 by volume) as eluent. The pure fractions are collected and the eluent is evaporated. The residue is crystallized from 2,2'-oxybispropane. The product is filtered off and dried, yielding 1-{3-[4-(diphenylmethyl)-1-piperazinyl]propyl}-1,3-dihydro-5-(trifluoromethyl)-2H-benzimidazol-2-one; mp. 152.7° C.

EXAMPLE LXXX

A mixture of 4 parts of 4,5-dichloro-$N^1$-{3-[4-(diphenylmethyl)-1-piperazinyl]propyl}-1,2-benzenediamine and 1.5 parts of urea is stirred for 3 hours in an oil-bath at 190° C. After cooling, water and trichloromethane are added. The layers are separated and the organic phase is dried, filtered and evaporated. The residue is purified by column-chromatography over silica gel using a mixture of trichloromethane and methanol (95:5 by volume) as eluent. The pure fractions are collected and the eluent is evaporated. The residue is crystallized from a mixture of methylbenzene and 2,2'-oxybispropane, yielding 5,6-dichloro-1-{3-[4-(diphenylmethyl)-1-piperazinyl]propyl}-1,3-dihydro-2H-benzimidazol-2-one; mp. 214.7° C.

EXAMPLE LXXXI

A mixture of 4.37 parts of N-(2-aminophenyl)-4-(diphenylmethyl)-1-piperazinepropanamine hydrochloride, 38 parts of carbon disulfide, 2 parts of sodium carbonate and 40 parts of ethanol is stirred and refluxed for 20 hours. The reaction mixture is evaporated and water is added to the residue. The precipitated product is filtered off, washed with water and dissolved in trichloromethane. The solution is dried, filtered and evaporated. The residue is crystallized from 4-methyl-2-pentanone, yielding 1-{3-[4-(diphenylmethyl)-1-piperazinyl]propyl}-1H-benzimidazole-2-thiol; mp 181.8° C.

EXAMPLE LXXXII

A mixture of 60 parts of N-(2-aminophenyl)-4-(diphenylmethyl)-1-piperazinepropanamine, 20 parts of methyl(iminomethoxymethyl)carbamate, 42 parts of acetic acid and 450 parts of trichloromethane is stirred and refluxed overnight. The reaction mixture is evaporated and the residue is stirred in water. The latter is decanted and the residue is taken up again in water. The whole is alkalized with a diluted ammonium hydroxide solution and the product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is crystallized from a mixture of 4-methyl-2-pentanone and 2,2'-oxybispropane, yielding methyl [1-{3-[4-(diphenylmethyl)-1-piperazinyl]propyl}-1H-benzimidazol-2-yl]carbamate; mp. 137.8° C.

A mixture of 12 parts of methyl [1-{3-[4-(diphenylmethyl)-1-piperazinyl]propyl}-1H-benzimidazol-2-yl]carbamate, 60 parts of a concentrated hydrochloric acid solution and 80 parts of ethanol is stirred and refluxed overnight. The reaction mixture is evaporated and water is added to the residue. The free base is liberated in the conventional manner with ammonium hydroxide and extracted with trichloromethane. The extract is dried, filtered and evaporated. The residue is crystallized from ethanol. The product is filtered off and dried, yielding 1-{3-[4-(diphenylmethyl)-1-piperazinyl]propyl}-1H-benzimidazol-2-amino; mp. 228.7° C.

A mixture of 10.7 parts of 1-{3-[4-(diphenylmethyl)-piperazinyl]propyl}-1H-benzimidazol-2-amine, 5.1 parts of acetic acid anhydride and 90 parts of methylbenzene is stirred and refluxed for 5 hours. The reaction mixture is evaporated and the residue is stirred in water. The whole is alkalized with ammonium hydroxide and the product is extracted with trichloromethane. The extract is dried, filtered and evaporated. The residue is crystallized from ethanol. The product is filtered off and dried, yielding N-[1-{3-[4-(diphenylmethyl)-1-piperazinyl]propyl}-1,3-dihydro-2H-benzimidazol-2-ylidene]acetamide; mp. 143.3° C.

EXAMPLE LXXXIII

A mixture of 2.3 parts of 1-{3-[4-(diphenylmethyl)-1-piperazinyl]propyl}-1,3-dihydro-2H-benzimidazol-2-one, 4.5 parts of formaldehyde solution 40% and 45 parts of N,N-dimethylformamide is stirred and heated for 2 hours at 100° C. The reaction mixture is cooled and diluted with water. The precipitated product is filtered off and crystallized from methylbenzene, yielding, after drying, 1-{3-[4-(diphenylmethyl)-1-piperazinyl]propyl}-1,3-dihydro-3-(hydroxymethyl)-2H-benzimidazol-2-one; mp. 102.5° C.

EXAMPLE LXXXIV

A mixture of 1.55 parts of acetic acid anhydride, 3 parts of 1-{3-[4-(diphenylmethyl)-1-piperazinyl]propyl}-1,3-dihydro-2H-benzimidazol-2-one and 22.5 parts of methylbenzene is stirred and refluxed overnight. Water is added to the reaction mixture and the layers are separated. The organic phase is dried, filtered and evaporated. The residue is purified by column-chromatography over silica gel using a mixture of trichloromethane and methanol (95:5 by volume) as eluent. The pure fractions are collected and the eluent is evaporated, yielding 1-acetyl-3-{3-[4-(diphenylmethyl)-1-piperazinyl]propyl}-1,3-dihydro-2H-benzimidazol-2-one; mp. 124.4° C.

EXAMPLE LXXXV

A mixture of 1.1 parts of ethyl 2-propenoate, 3 parts of 1-{3-[4-(diphenylmethyl)-1-piperazinyl]propyl}-1,3-dihydro-2H-benzimidazol-2-one, a few drops of a N,N,N-trimethylbenzenemethanaminium hydroxide solution 40% in methanol and 25 parts of 1,4-dioxane is stirred and refluxed for 24 hours. The reaction mixture is evaporated. The residue is purified by column-chromatography over silica gel using a mixture of trichloromethane and methanol (95:5 by volume) as eluent. The pure fractions are collected and the eluent is evaporated. The residue is converted into the hydrochloride salt in 2-propanol and ethanol. The salt is filtered off and dried, yielding ethyl 3-{3-[4-(diphenylmethyl)-1-piperazinyl]propyl}-2,3-dihydro-2-oxo-1H-benzimidazole-1-propanoate dihydrochloride. dihydrate; mp. 204° C.

EXAMPLE LXXXVI

A mixture of 3 parts of 1-{3-[4-(diphenylmethyl)-1-piperazinyl]propyl}-1,3-dihydro-2H-benzimidazol-2-one, 1 part of isocyanatomethane and 25 parts of 1,4-dioxane is stirred and refluxed overnight. The reaction mixture is evaporated and the residue is purified by column-chromatography over silica gel using a mixture of trichloromethane and methanol (95:5 by volume) as eluent. The pure fractions are collected and the eluent is evaporated. The residue is crystallized from a mixture of methylbenzene and 2,2'-oxybispropane, yielding 3-{3-[4-(diphenylmethyl)-1-piperazinyl]propyl}-2,3-dihydro-N-methyl-2-oxo-1H-benzimidazole-1-carboxamide; mp. 153.1° C.

EXAMPLE LXXXVII

A mixture of 4.8 parts of 1-(3-chloropropyl)-1,3-dihydro-2H-benzimidazol-2-one, 6.1 parts of 4-(diphenylmethoxy)piperidine hydrochloride, 7.5 parts of sodium carbonate and 200 parts of 4-methyl-2-pentanone is stirred and refluxed overnight with water-separator. The reaction mixture is cooled and water is added. The layers are separated and the 4-methyl-2-pentanone-phase is dried, filtered and evaporated. The oily residue is purified by column-chromatography over silica gel using a mixture of trichloromethane and 5% of methanol as eluent. The pure fractions are collected and the eluent is evaporated. The residue is crystallized from 4-methyl-2-pentanone, yielding 1-{3-[4-(diphenylmethoxy)-1-piperidinyl]propyl}-1,3-dihydro-2H-benzimidazol-2-one; mp. 149.2° C.

EXAMPLE LXXXVIII

Following the procedure of Example LXXXVII and using equivalent amounts of the appropriate starting materials, the following compounds are obtained in free base form or in the form of a hydrochloride salt after treatment of the base with hydrochloric acid.
1-{2-[4-(diphenylmethoxy)-1-piperidinyl]ethyl}-1,3-dihydro-2H-benzimidazol-2-one hydrochloride; mp. 253.1° C.;

1-[3-{4-[bis(4-fluorophenyl)methoxy]-1-piperidinyl}-propyl]-1,3-dihydro-2H-benzimidazol-2-one hydrochloride. hemihydrate; mp. 167.2° C.;

1-[2-{4-[bis(4-fluorophenyl)methoxy]-1-piperidinyl}ethyl]-1,3-dihydro-2H-benzimidazol-2-one hydrochloride. hemihydrate; mp. 251.4° C.; and 1-{4-[4-(diphenylmethyl)-1-piperidinyl]butyl}-1,3-dihydro-2H-benzimidazol-2-one; mp. 152° C.

EXAMPLE LXXXIX

A mixture of 6 parts of 1-(3-chloropropyl)-1H-benzimidazole, 7.6 parts of 4-(diphenylmethoxy)piperidine hydrochloride, 10.6 parts of sodium carbonate and 200 parts of 4-methyl-2-pentanone is stirred and refluxed overnight with water-separator. The reaction mixture is cooled, water is added and the layers are separated. The 4-methyl-2-pentanone-phase is dried, filtered and evaporated. The oily residue is purified by column-chromatography over silica gel using a mixture of trichloromethane and methanol (95:5 by volume) as eluent. The pure fractions are collected and the eluent is evaporated. The oily residue is crystallized from 2,2'-oxybispropane. The product is filtered off and dried, yielding 1-{3-[4-(diphenylmethoxy)-1-piperidinyl]propyl}-1H-benzimidazole; mp. 110.2° C.

EXAMPLE XC

A mixture of 13 parts of 1,3-dihydro-1-[3-(1-piperazinyl)propyl]-2H-benzimidazol-2-one, 12.4 parts of 1,1'-(bromomethylene)bis[benzene], 6.6 parts of sodium carbonate and 200 parts of 4-methyl-2-pentanone is stirred and refluxed overnight with water-separator. After cooling to room temperature, water is added and the layers are separated. The organic layer is dried, filtered and evaporated. The residue is crystallized from a mixture of 2,2'-oxybispropane and a small amount of 2-propanol, yielding 1-{3-[4-(diphenylmethyl)-1-piperazinyl]propyl}-1,3-dihydro-2H-benzimidazol-2-one; mp. 153° C.

EXAMPLE XCI

Following the procedure of Example XC and using equivalent amounts of the appropriate starting materials, the following compounds are prepared:

1-[2-{4-[bis(4-fluorophenyl)methyl]-1-piperazinyl}ethyl]-1,3-dihydro-2H-benzimidazol-2-one hemihydrate; mp. 131.5° C.;

1-{2-[4-(diphenylmethyl)-1-piperazinyl]ethyl}-1,3-dihydro-2H-benzimidazol-2-one; mp. 218° C.; and 1-[3-{4-[bis(4-fluorophenyl)methyl]-1-piperazinyl}-propyl]-1,3-dihydro-2H-benzimidazol-2-one; mp. 198° C.

EXAMPLE XCII

A mixture of 5.2 parts of 1,3-dihydro-1-[3-(1-piperazinyl)propyl]-2H-benzimidazol-2-one, 5.28 parts of 2-(chlorophenylmethyl)pyridine hydrochloride, 5.3 parts of sodium carbonate and 90 parts of N,N-dimethylformamide is stirred and heated overnight at 50° C. The reaction mixture is cooled and poured onto ice-water. The product is extracted with methylbenzene. The extract is dried, filtered and evaporated. The residue is crystallized from a mixture of 4-methyl-2-pentanone and 2,2'-oxybispropane. The product is filtered off and dried, yielding 2 parts (23.4%) of 1,3-dihydro-1-[3-{4-[phenyl(2-pyridinyl)methyl]-1-piperazinyl}propyl]-2H-benzimidazol-2-one; mp. 141.7° C.

EXAMPLE XCIII

Following the procedure of Example XCII and using equivalent amounts of the appropriate starting materials, the following compounds are prepared:

1-[3-{4-[(4-fluorophenyl)(3-pyridinyl)methyl]-1-piperazinyl}propyl]-1,3-dihydro-2H-benzimidazol-2-one; mp. 154.1° C.;

1,3-dihydro-1-[3-{4-[phenyl(3-pyridinyl)methyl]-1-piperazinyl}propyl]-2H-benzimidazol-2-one; mp. 162.6° C.;

1-[3-{4-[(4-fluorophenyl)-(4-methylphenyl)methyl]-1-piperazinyl}propyl]-1,3-dihydro-2H-benzimidazol-2-one; mp. 147.8° C.;

1-[3-{4-[bis(4-chlorophenyl)methyl]-1-piperazinyl}-propyl]-1,3-dihydro-2H-benzimidazol-2-one; mp. 209.5° C.;

1-[3-{4-[(2,4-dichlorophenyl)(4-fluorophenyl)methyl]-1-piperazinyl}propyl]-1,3-dihydro-2H-benzimidazol-2-one; mp. 160.1° C.;

1-[3-{4-[(2,3-dimethylphenyl)phenylmethyl]-1-piperazinyl}propyl]-1,3-dihydro-2H-benzimidazol-2-one; mp. 169.8° C.;

1,3-dihydro-1-{3-[4-{(4-methoxyphenyl)[3-(trifluoromethyl)phenyl]methyl}-1-piperazinyl]propyl}-2H-benzimidazol-2-one; mp. 153.4° C.;

1,3-dihydro-1-[3-{4-[(4-methylphenyl)phenylmethyl]-1-piperazinyl}propyl]-2H-benzimidazol-2-one; mp. 178.3° C.;

1-[3-{4-[(2,4-dimethylphenyl)phenylmethyl]-1-piperazinyl}propyl]-1,3-dihydro-2H-benzimidazol-2-one; mp. 115.8° C.; and 1-[3-{4-[(2,5-dimethylphenyl)phenylmethyl]-1-piperazinyl}propyl]-1,3-dihydro-2H-benzimidazol-2-one; mp. 156.3° C.

EXAMPLE XCIV

50 Parts of 1-{3-[4-(diphenylmethyl)-1-piperazinyl]propyl}-1,3-dihydro-2H-benzimidazol-2-one are dissolved in 200 of 2-propanol while stirring and heating. The solution is stirred with 2.5 parts of activated charcoal. The latter is filtered off and upon cooling to room temperature, the product is crystallized. It is filtered off and converted into the hydrochloride salt in 2-propanol. The salt is filtered off, washed twice with 2-propanol and dried overnight in vacuo at 60° C. It is dissolved in 320 parts of methanol and the free base is liberated in the conventional manner with a sodium hydroxide solution 5 N. The whole is concentrated to a volume of about 150 parts. The precipitated product is filtered off, washed with 500 parts of water and dissolved in 120 parts of 2-propanol. The solution is stirred and heated with 1 part of activated charcoal. The latter is filtered off over hyflo while hot. The filtrate is cooled to room temperature while stirring. The precipitated product is filtered off and dried over week-end in vacuo at 60° C., yielding 21.49 parts of 1{3-[4-(diphenylmethyl)-1-piperazinyl]propyl}-1,3-dihydro-2H-benzimidazol-2-one hydrate; mp. 156.6° C.

EXAMPLE XCV

To a stirred mixture of 9.4 parts of 1-{3-[4-(diphenylmethyl)-1-piperazinyl]propyl}-1,3-dihydro-2H-benzimidazol-2-one and 180 parts of methylbenzene are added 0.8 parts of sodium hydride dispersion 75% and the whole is stirred and heated for 60 minutes at 90° C. After cooling to 30° C., 0.2 parts of 2,3,11,12-dibenzo-1,4,7,10,13,16-hexaoxacyclooctadeca-2,11-diene are added and stirring is continued for 10 minutes. Then there are added 4.2 parts of ethyl 2-bromoacetate and the mixture is stirred and refluxed overnight. The reaction mixture is cooled to 90° C., 50 parts of water are added and the layers are separated while hot. The organic phase is evaporated, yielding 10 parts of ethyl 3-{3-[4-(diphenylmethyl)-1-piperazinyl]propyl}-2,3-dihydro-2-oxo-1H-benzimidazole-1-acetate as a residue.

EXAMPLE XCVI

A mixture of 9.8 parts of ethyl 3-{3-[4-(diphenylmethyl)1-piperazinyl]propyl}-2,3-dihydro-2-oxo-1H-benzimidazole-1-acetate, 1.2 parts of sodium hydroxide and 150 parts of water is stirred and refluxed for 5 minutes (+80° C.). The reaction mixture is filtered and the filtrate is acidified with acetic acid to pH 5.8-6: a sticky precipitate is formed. It is separated and crystallized from ethanol and water. The product is filtered off and dried in vacuo at 100° C. for 3 hours, yielding 6 parts of 3-{3-[4-(diphenylmethyl)-1-piperazinyl]propyl}-2,3-dihydro-2-oxo-1H-benzimidazole-1-acetic acid hemihydrate; mp. 138.7° C.

We claim:

1. A chemical compound selected from the group consisting of a compound having the formula

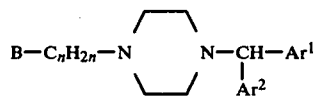

and the pharmaceutically acceptable acid addition salts thereof, wherein:
   $Ar^1$ and $Ar^2$ are each independently selected from the group consisting of phenyl, substituted phenyl and pyridinyl, wherein said substituted phenyl is phenyl having from 1 to 2 substituents independently selected from the group consisting of halo, lower alkyl, lower alkyloxy, trifluoromethyl and nitro;
   n is an integer of from 2 to 6 inclusive, provided that when $C_nH_{2n}$ represents a branched alkylene chain, then at least 2 carbon atoms are present in the linear portion of the chain linking B with the piperazine nitrogen atom; and
   B is a radical having the formula

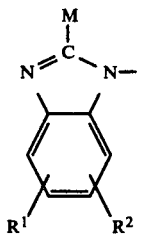

wherein:
   $R^1$ and $R^2$ are each independently selected from the group consisting of hydrogen, halo, lower alkyl and trifluoromethyl; and
   M is a member selected from the group consisting of phenyl, phenylmethyl, mercapto, lower alkylthio, amino, lower alkylcarbonylamino, lower alkyloxycarbonylamino, and cycloalkyl having from 3 to 6 carbon atoms.

2. A pharmaceutical composition comprising an inert carrier material and as an active ingredient an effective antihistaminic or anti-anaphylactic amount of a chemical compound selected from the group consisting of a compound having the formula

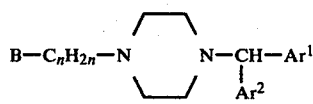

and the pharmaceutically acceptable acid addition salts thereof, wherein:
   $Ar^1$ and $Ar^2$ are each independently selected from the group consisting of phenyl, substituted phenyl and pyridinyl, wherein said substituted phenyl is phenyl having from 1 to 2 substituents independently selected from the group consisting of halo, lower alkyl, lower alkyloxy, trifluoromethyl and nitro;
   n is an integer of from 2 to 6 inclusive, provided that when $C_nH_{2n}$ represents a branched alkylene chain, then at least 2 carbon atoms are present in the linear portion of the chain linking B with the piperazine nitrogen atom; and
   B is a radical having the formula

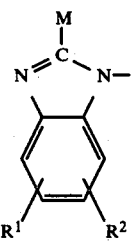

wherein:
   $R^1$ and $R^2$ are each independently selected from the group consisting of hydrogen, halo, lower alkyl, and trifluoromethyl; and
   M is a member selected from the group consisting of phenyl, phenylmethyl, mercapto, lower alkylthio, amino, lower alkylcarbonylamino, lower alkyloxycarbonylamino, and cycloalkyl having from 3 to 6 carbon atoms.

3. A method of producing antihistaminic or anti-anaphylactic activity in a warm-blooded animal in need of same which comprises systemic administration to said warm-blooded animal of an effective antihistaminic or anti-anaphylactic amount of a chemical compound selected from the group consisting of a compound having the formula

and the pharmaceutically acceptable acid addition salts thereof, wherein:
   $Ar^1$ and $Ar^2$ are each independently selected from the group consisting of phenyl, substituted phenyl and pyridinyl, wherein said substituted phenyl is phenyl having from 1 to 2 substitutents independently selected from the group consisting of halo, lower alkyl, lower alkyloxy, trifluoromethyl and nitro;

n is an integer of from 2 to 6 inclusive, provided that when $C_nH_{2n}$ represents a branched alkylene chain, then at least 2 carbon atoms are present in the linear portion of the chain linking B with the piperazine nitrogen atom; and B is a radical having the formula

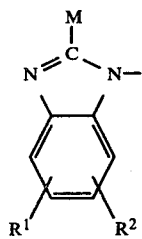

wherein:

$R^1$ and $R^2$ are each independently selected from the group consisting of hydrogen, halo, lower alkyl, and trifluoromethyl; and M is a member selected from the group consisting of hydrogen, lower alkyl, phenyl, phenylmethyl, mercapto, lower alkylthio, amino, lower alkylcarbonylamino, lower alkyloxycarbonylamino, and cycloalkyl having from 3 to 6 carbon atoms.

4. A method of producing antihistaminic or anti-anaphylactic activity in a warm-blooded animal in need of same which comprises systemic administration to said warm-blooded animal of an effective antihistaminic or anti-anaphylactic amount of a chemical compound selected from the group consisting of 1-{3-[4-(diphenylmethyl)-1-piperazinyl]propyl}-1H-benzimidazole and the pharmaceutically acceptable acid addition salts thereof.

5. A method of producing antihistaminic or anti-anaphylactic activity in a warm-blooded animal in need of same which comprises systemic administration to said warm-blooded animal of an effective antihistaminic or anti-anaphylactic amount of a chemical compound selected from the group consisting of 1-[4-{4-[(4-fluorophenyl)phenylmethyl]-1-piperazinyl}butyl]-1H-benzimidazole and the pharmaceutically acceptable acid addition salts thereof.

6. A method of producing antihistaminic or anti-anaphylactic activity in a warm-blooded animal in need of same which comprises systemic administration to said warm-blooded animal of an effective antihistaminic or anti-anaphylactic amount of a chemical compound selected from the group consisting of 1-[4-{4-[bis(4-fluorophenyl)methyl]-1-piperazinyl}butyl]-1H-benzimidazole and the pharmaceutically acceptable acid addition salts thereof.

* * * * *